US012688556B2

(12) United States Patent
Kim

(10) Patent No.: US 12,688,556 B2
(45) Date of Patent: Jul. 21, 2026

(54) METHOD FOR THREE-DIMENSIONALLY MODELING EYEBALL AND OPTIC NERVES USING MERGING OF MRI IMAGES AND OCT IMAGES

(71) Applicant: THE CATHOLIC UNIVERSITY OF KOREA INDUSTRY-ACADEMIC COOPERATION FOUNDATION, Seoul (KR)

(72) Inventor: Yong Chan Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 255 days.

(21) Appl. No.: 18/681,197

(22) PCT Filed: Aug. 31, 2022

(86) PCT No.: PCT/KR2022/013000
§ 371 (c)(1),
(2) Date: Feb. 5, 2024

(87) PCT Pub. No.: WO2023/038359
PCT Pub. Date: Mar. 16, 2023

(65) Prior Publication Data
US 2024/0281934 A1 Aug. 22, 2024

(30) Foreign Application Priority Data
Sep. 10, 2021 (KR) ........................ 10-2021-0121288

(51) Int. Cl.
G06T 5/50 (2006.01)
A61B 3/00 (2006.01)
G06T 7/00 (2017.01)

(52) U.S. Cl.
CPC .............. G06T 5/50 (2013.01); A61B 3/0025 (2013.01); G06T 7/0012 (2013.01);
(Continued)

(58) Field of Classification Search
CPC ..................... G06T 5/50; G06T 7/0012; G06T 2207/10088; G06T 2207/10101;
(Continued)

(56) References Cited

U.S. PATENT DOCUMENTS 11,432,719 B2 * 9/2022 Huang ..................... G06T 7/168
2007/0115481 A1 * 5/2007 Toth ..................... A61B 3/0025
356/497

FOREIGN PATENT DOCUMENTS

JP 2018-149449 A 9/2018
KR 10-1095302 B1 12/2011
(Continued)

OTHER PUBLICATIONS

The Connective Tissue Components of Optic Nerve Head Cupping in Monkey Experimental Glaucoma Part 1: Global Change (Year: 2015).*
(Continued)

*Primary Examiner* — Jennifer Mehmood
*Assistant Examiner* — Pardis Sohraby
(74) *Attorney, Agent, or Firm* — Bridgeway IP Law Group, PLLC; Jihun Kim

(57) ABSTRACT

A method for three-dimensionally modeling an eyeball and optical nerves using the merging of MRI images and OCT images, comprises: (a) a step for three-dimensionally modeling an eyeball model on the basis of the shapes of an eyeballs in a first MRI head image and a second MRI head image; (b) a step for three-dimensionally modeling an ASCO model in a corrected OCT eyeball cross-sectional image; (c) a step for three-dimensionally modeling the
(Continued)

lamina cribrosa in the corrected OCT eyeball image; and (d) a step for generating an optic nerve model by three-dimensionally modeling an optic tract connected to the three-dimensionally modeled eyeball model.

10 Claims, 36 Drawing Sheets

(52) U.S. Cl.
CPC .............. *G06T 2207/10088* (2013.01); *G06T 2207/10101* (2013.01); *G06T 2207/30041* (2013.01)

(58) Field of Classification Search
CPC . G06T 2207/30041; G06T 17/00; G06T 7/12; G06T 17/20; G06T 19/00; A61B 3/0025
USPC ........................................................ 382/128
See application file for complete search history.

(56) References Cited

FOREIGN PATENT DOCUMENTS

| KR | 10-2045620 B1 | 11/2019 |
| KR | 10-2112408 B1 | 5/2020 |
| WO | 2019-074077 A1 | 4/2019 |

OTHER PUBLICATIONS

Kyoung Min Lee et al., "Relationship between Three-Dimensional Magnetic Resonance Imaging Eyeball Shape and Optic Nerve Head Morphology", American Academy of Ophthalmology, Apr. 2021, pp. 532-544, vol. 128, Issue 4.

Seungwoo Hong et al., "OCT-Detected Optic Nerve Head Neural Canal Direction, Obliqueness and Minimum Cross-Sectional Area in Healthy Eyes", American Journal of Ophthalmology, Dec. 2019, pp. 185-205, vol. 208.

* cited by examiner (a)

(b)

(1) ● Retinal Peak (RP)
(2) ○ Bruch's Membrane Opening (BMO)
(3) ● Anterior Sclera Canal Opening (ASCO)
(4) ● Posterior Sclera Canal Opening (PSCO)
(5) ● Anterior-most aspect of the SubArachnoid Space (ASAS)
(6) ● Dura Path (DP)
(7) ● Optical Nerve Path (ONP)
(8) ● Dura Joint
  ⌢ Lamina Cribrosa (LC)

(a)

(b)

(1)● Retinal Peak (RP)
(2)○ Bruch's Membrane Opening (BMO)
(3)● Anterior Sclera Canal Opening (ASCO)
(4)● Posterior Sclera Canal Opening (PSCO)
(5)● Anterior-most aspect of the SubArachnoid Space (ASAS)
(6)● Dura Path (DP)
(7)● Optical Nerve Path (ONP)
(8)● Dura Joint
〜〜〜 Lamina Cribrosa (LC)

(a)

(b)

(c)

(d)

(a)

cross-section
of eyeball (b)    intersection
point cross-section of (a) eyeball corrected OCT cross-sectional image (b)

(a)

(b)

cross-section of
eyeball (a)

cross-section of
eyeball corrected OCT
cross-sectional
image (b)

cross-section of
eyeball corrected OCT
cross-sectional
image (c)

(a)

(b)

(a)

(b)

(a)

(b)

(a)                  (b)

(a)

(b)

Cross-section of
eyeball

Corrected OCT
cross-sectional
image

Optic nerve
model

METHOD FOR THREE-DIMENSIONALLY MODELING EYEBALL AND OPTIC NERVES USING MERGING OF MRI IMAGES AND OCT IMAGES

CROSS-REFERENCE TO RELATED APPLICATION

This application claims priority to and the benefit of Korean Patent Application No. 10-2021-0121288 filed in the Korean Intellectual Property Office on Sep. 10, 2021, the entire contents of which are incorporated herein by reference.

TECHNICAL FIELD

The present invention relates to a method for three-dimensionally modeling an eyeball and an optic nerve using a merge of an MRI image and an OCT image. More specifically, the present invention relates to a method for three-dimensionally modeling an eyeball and an optic nerve using a merge of an MRI image and an OCT image, by matching corrected OCT cross-sectional image of an eyeball with an MRI image, and then three-dimensionally modeling the eyeball, a connection part between the eyeball and the optic nerve, and the optic nerve.

BACKGROUND ART

There are many ophthalmic diseases that affect optic nerve, the most representative of which is glaucoma, which causes damage to the optic nerve and impairs the vision field in a characteristic pattern due to risk factors such as elevated intraocular pressure. Glaucoma leaves permanent loss of visual field to a patient unless diagnosed and treated properly at the early stage. Therefore, it is important to detect several variants associated with glaucoma and treat them early. In particular, in the case of glaucoma with intraocular pressure in a normal range, unlike glaucoma with elevated intraocular pressure or accompanied by other ocular diseases, there is a high possibility of missing an early diagnosis of the glaucoma.

Various tests such as ophthalmoscopy, stereography, and perimetry test have been performed for the early diagnosis of glaucoma. Among them, optic nerve examination using the ophthalmoscopy and stereography had the disadvantages that it was difficult to detect subtle initial changes and the evaluation was subjective. The perimetry test is a more objective test, but studies have shown that about 40% of retinal ganglion cells are already damaged before abnormalities appear on the perimetry test, so the perimetry test has limitations in its function as an early diagnosis of glaucoma.

Accordingly, various tests for the early diagnosis of glaucoma have been proposed, and interest in glaucomatous changes in the stage before abnormalities appear on the perimetry test has increased.

Among various changes associated with glaucoma, it has been reported that the change in the retinal nerve fiber layer (RNFL) precedes the change in the optic disk and vision field. Accordingly, some opinions suggest that it is useful to examine the RNFL for the early diagnosis of glaucoma.

Several equipment have been developed to examine changes in the RNFL. Optical coherence tomography (OCT) and scanning laser polarimetry are equipment which quantify the thickness of the RNFL reflected at the retina-vitreous border, and measure the thickness of four peripapillary sectors in upper, lower, nose and ear directions, the thickness of each of the twelve clock-hour sectors, and the average of all the obtained thickness. According to several research results, the retinal nerve fiber layer measured using the OCT and the scanning laser polarimetry becomes thinner in areas consistent with visual field defects, so it is known that measurement of the RNFL thickness using the OCT is helpful in the early diagnosis of glaucoma.

In general, the diagnosis of glaucoma using the OCT and the scanning laser polarimetry is made by comparing the measured thickness of the RNFL with that of a normal person. However, the thickness of the RNFL of normal people differs depending on the area in each person, and the average thickness of the RNFL of normal people also varies greatly depending on areas, so there is a problem that the sensitivity and specificity of diagnosis are poor in the case of early-stage glaucoma.

(Patent Document 1) KR Registered Patent No. 10-2045620 (2019 Nov. 11)

(Patent Document 2) KR Registered Patent No. 10-1095302 (2011 Dec. 12)

DISCLOSURE

Technical Problem

In order to solve the above problems, an object of the present invention is to provide a method for three-dimensionally modeling an eyeball and an optic nerve using a merge of an MRI image and an OCT image, which can help practitioners accurately diagnose and predict the possibility of lesions such as myopia and glaucoma through an eyeball model, an ASCO model, an LC model, and an optic nerve model that mimics the actual eyeball, by matching an OCT cross-sectional image of the eyeball to the optic disk of a low-resolution MRI head image, which can image the eyeball and the optic nerve, and then three-dimensionally modeling the eyeball, a connection part between the eyeball and the optic nerve, and the optic nerve.

Technical Solution

The technical objects to be achieved by the present invention are not limited to the technical objects mentioned above, and other technical objects not mentioned may be clearly understood by those skilled in the art from the following descriptions.

In order to achieve the above object, the configuration of the present invention provides a method for three-dimensionally modeling an eyeball and an optic nerve using a merge of an MRI image and an OCT image comprising the steps of: (a) three-dimensionally modeling an eyeball model based on a shape of an eyeball in first and second MRI head images; (b) three-dimensionally modeling an ASCO model in a corrected OCT cross-sectional image of the eyeball; (c) three-dimensionally modeling lamina cribrosa (LC) in a corrected OCT eyeball image; and (d) generating an optic nerve model by three-dimensionally modeling an optic nerve path connected to the three-dimensionally modeled eyeball model, wherein the first MRI head image is an MRI head image with the largest eyeball among a plurality of the first MRI head images, each image being sliced in a XY plane, and the second MRI head image is an MRI head image with the largest eyeball among a plurality of the second MRI head images, each image being sliced in a XZ plane.

In an embodiment of the present invention, the step (a) may comprise the steps of (a1) forming a gaze reference line passing through a center of the eyeball and a center of an iris in the MRI head image with a larger inscribed circle inscribed on the eyeball, among the first MRI head image and the second MRI head image; (a2) forming a plurality of first reference planes perpendicular to the gaze reference line; (a3) forming a plurality of first ellipses on the plurality of first reference planes spaced apart from each other; and (a4) forming an ocular surface surrounding the plurality of first ellipses, wherein the plurality of first ellipses are asymmetrical ellipses that become smaller toward both sides from the first ellipse located at the center of the eyeball among the plurality of first ellipses, based on an eyeball shape of the plurality of first MRI head images and an eyeball shape of the plurality of second MRI head images.

In an embodiment of the present invention the step (a) may further comprise the steps of (a5) forming a BMO layer with a thickness of 0.004 mm from an inner surface of an ocular surface; (a6) sequentially forming choroid and sclera with a predetermined thickness from an outer surface of the ocular surface; and (a7) generating the eyeball model that is three-dimensionally modeled.

In an embodiment of the present invention, the step (b) may comprise the steps of (b1) marking Bruch's Membrane Opening (BMO), choroid Opening, and ASCO on the corrected OCT cross-sectional image of the eyeball; (b2) forming a BMO line, a choroid opening line, and an ASCO line to distinguish a Bruch's Membrane Opening (BMO) layer, a choroid opening layer, and an ASCO layer in the corrected OCT cross-sectional image of the eyeball; (b3) forming a normal line perpendicular to the BMO line, choroid opening line, and ASCO line and then forming a vertical plane perpendicular to the normal line; and (b4) three-dimensionally modeling the ASCO model by connecting the vertical plane through which a central part penetrates and the ASCO line.

In an embodiment of the present invention, the step (c) may comprise the steps of (c1) forming a cross-section of Lamina Cribrosa (LC) on the corrected OCT cross-sectional image of the eyeball, (c2) forming a reference plane for forming the Lamina Cribrosa (LC), and (c3) three-dimensionally modeling the Lamina Cribrosa (LC) from the reference plane.

In an embodiment of the present invention, the step (d) may comprise the steps of (d1) obtaining a center point of an optic nerve root based on the first MRI head image and the second MRI head image; (d2) forming a second connection line connecting the center point of the optic nerve root with a pair of ASCOs; and (d3) forming a plurality of second reference planes dividing the second connection line into five equal parts.

In an embodiment of the present invention, the step (d) may further comprise the steps of (d4) forming the plurality of second ellipses on the plurality of second reference planes based on the first MRI head image and the second MRI head image, (d5) forming a reference line connecting the centers of the plurality of second ellipses, and (d6) forming an optic nerve path surrounding the plurality of second ellipses along the reference line.

In an embodiment of the present invention, the step (d) may further comprise the steps of (d7) extending an end of the optic nerve path to sclera; (d8) forming an interior of the optic nerve path by reflecting a preset thickness of the optic nerve path; and (d9) forming the three-dimensionally modeled optic nerve model.

Advantageous Effects

The effect of the present invention according to the above configuration is that it can help practitioners accurately diagnose and predict the possibility of lesions such as myopia and glaucoma through an eyeball model, an ASCO model, an LC model, and an optic nerve model that mimics the actual eyeball, by matching an OCT cross-sectional image of the eyeball to the optic disk of a low-resolution MRI head image, which can image the eyeball and the optic nerve, and then three-dimensionally modeling the eyeball, a connection part between the eyeball and the optic nerve, and the optic nerve.

The effects of the present disclosure are not limited to the above-mentioned effects, and it should be understood that the effects of the present disclosure include all effects that could be inferred from the configuration of the invention described in the detailed description of the invention or the appended claims.

Figure 5:
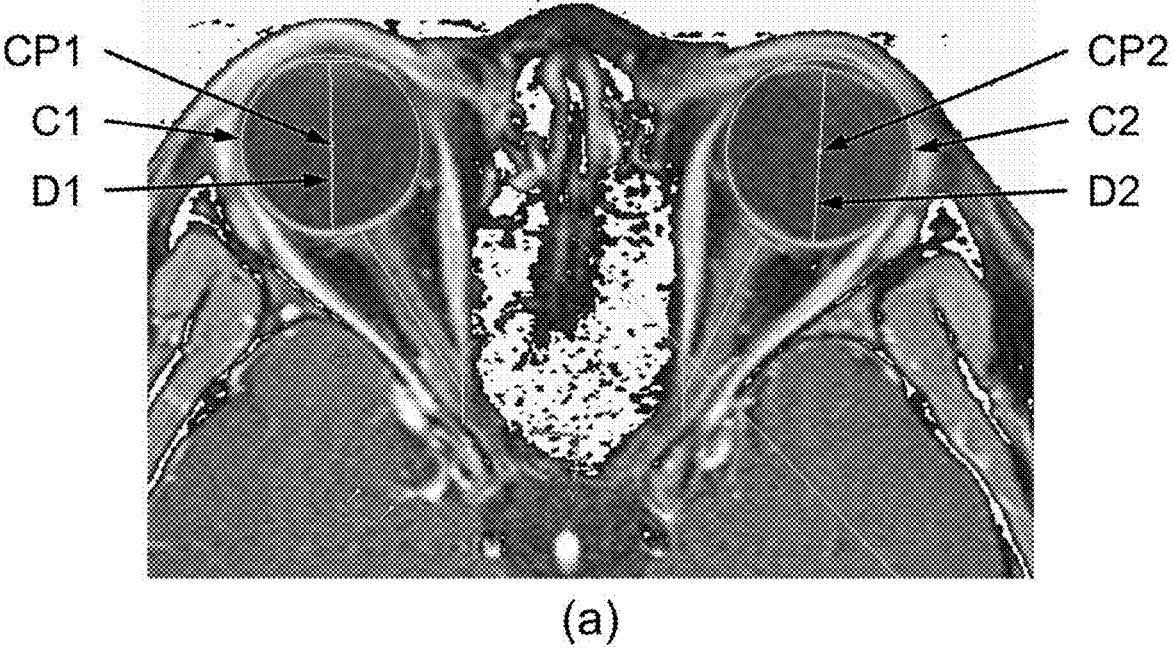
Figure 5:
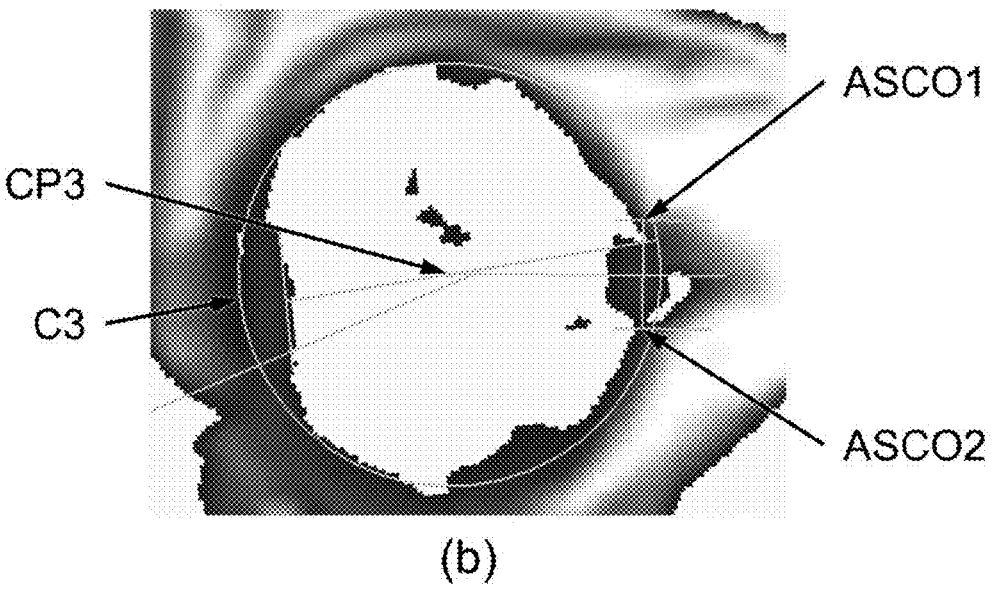

(a) of FIG. 5 is a diagram showing a first MRI head image with a largest eyeball among a plurality of first MRI head images sliced in the XY plane.

(b) of FIG. 5 is a diagram showing a second MRI head image with a largest eyeball among a plurality of second MRI head images sliced in the XZ plane.

Figure 6:
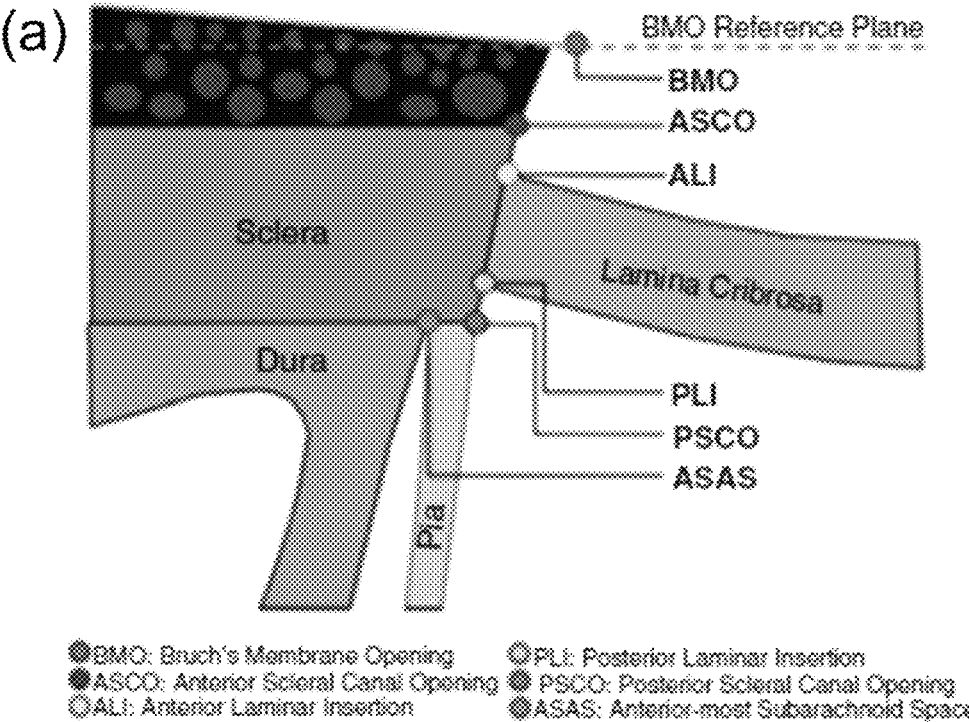
Figure 6:
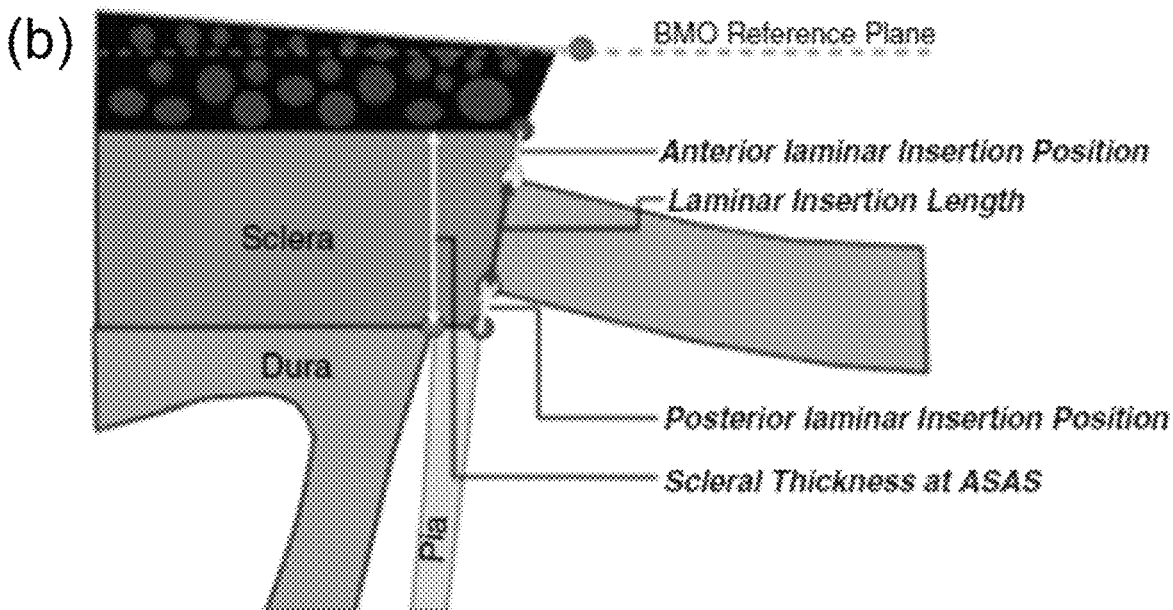

(a) and (b) of FIG. 6 are conceptual diagrams showing the elements that constitute an eyeball and an optic nerve and optic nerve measurement points.

Figure 7:
Figure 7:
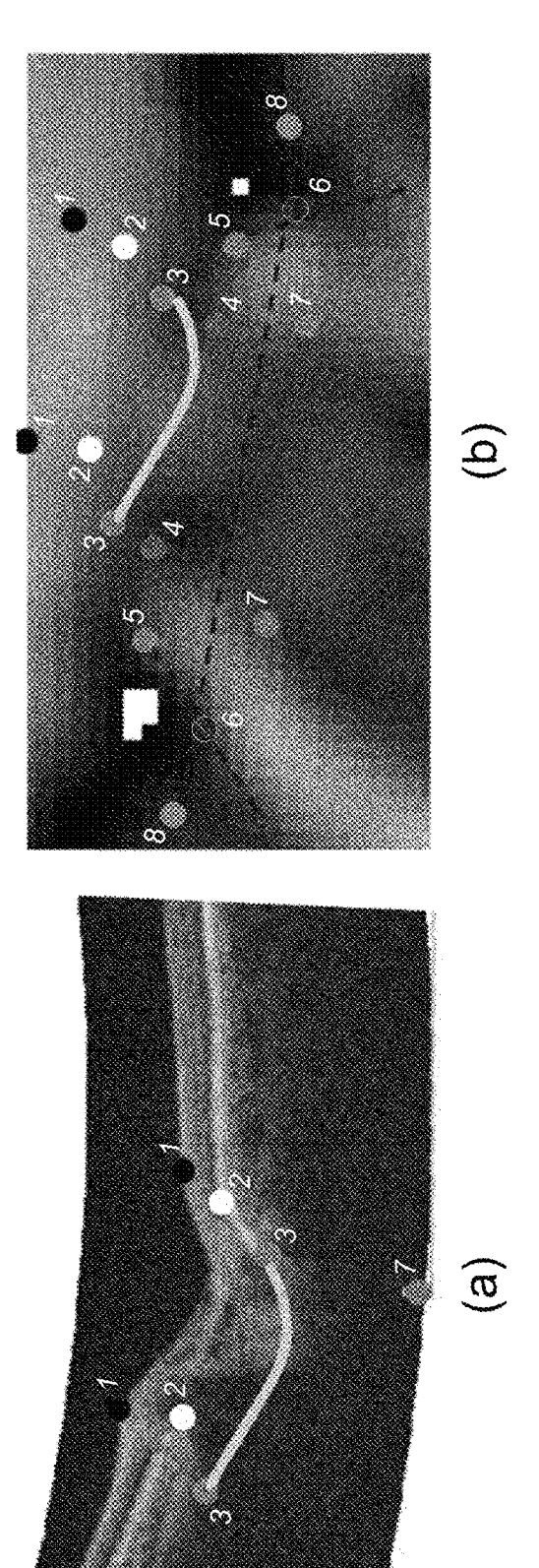

(a) and (b) of FIG. 7 are conceptual diagrams showing optic nerve measurement points.

Figure 8:
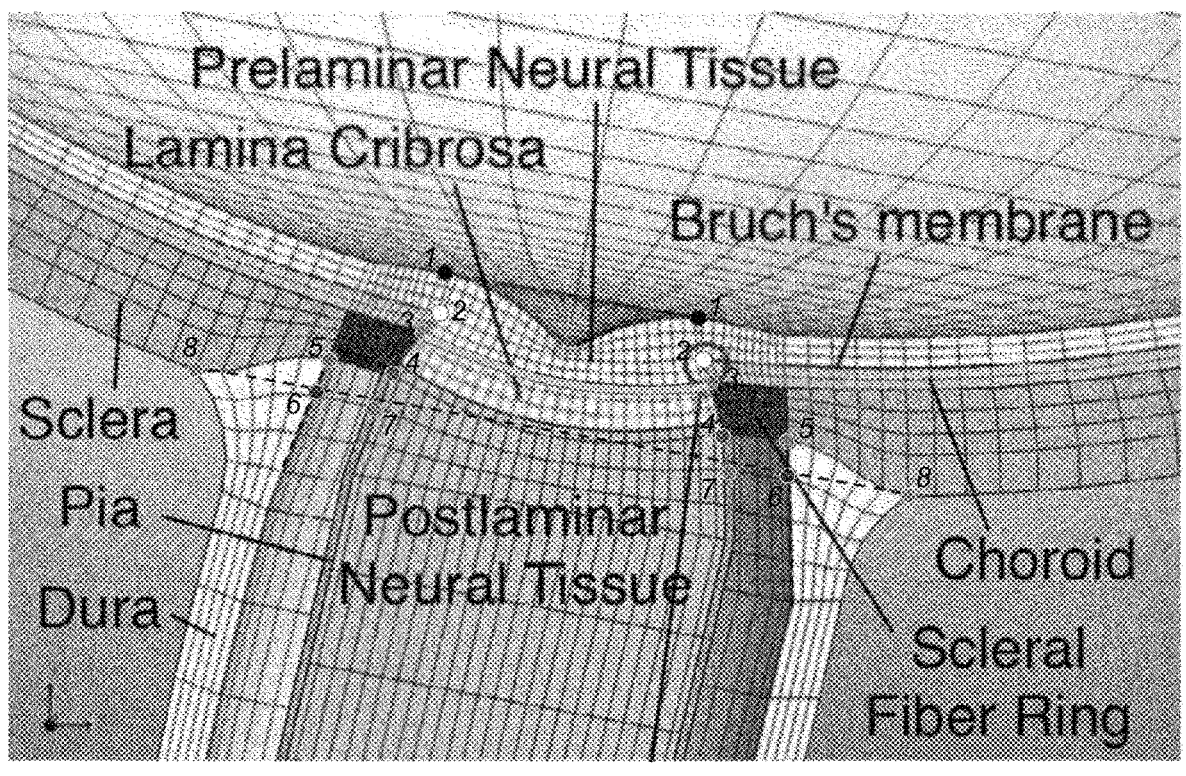

FIG. 8 is a diagram showing the results of analysis of the elements that constitute an eyeball and an optic nerve.

Figure 9:
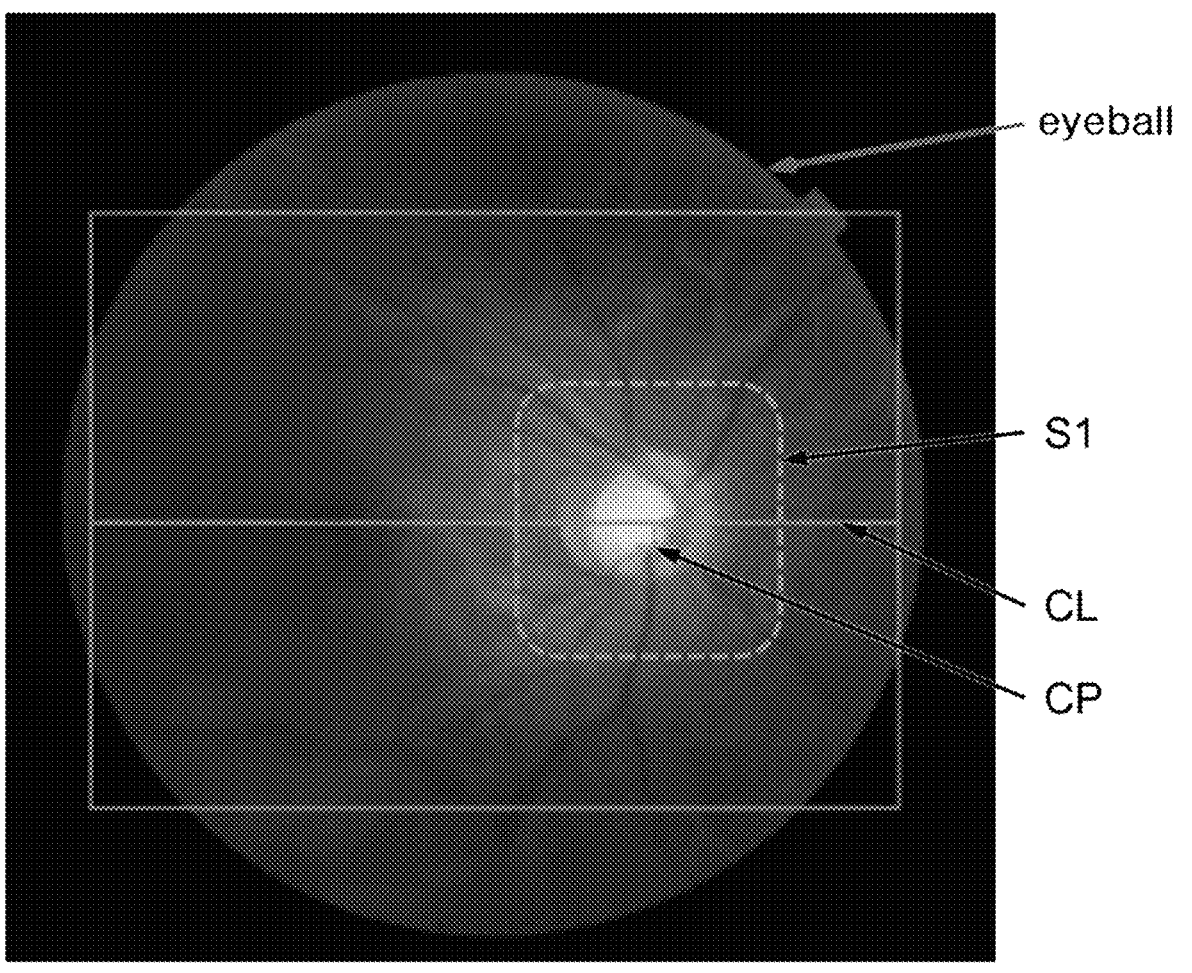

FIG. 9 is a diagram showing an OCT eyeball image.

Figure 10:
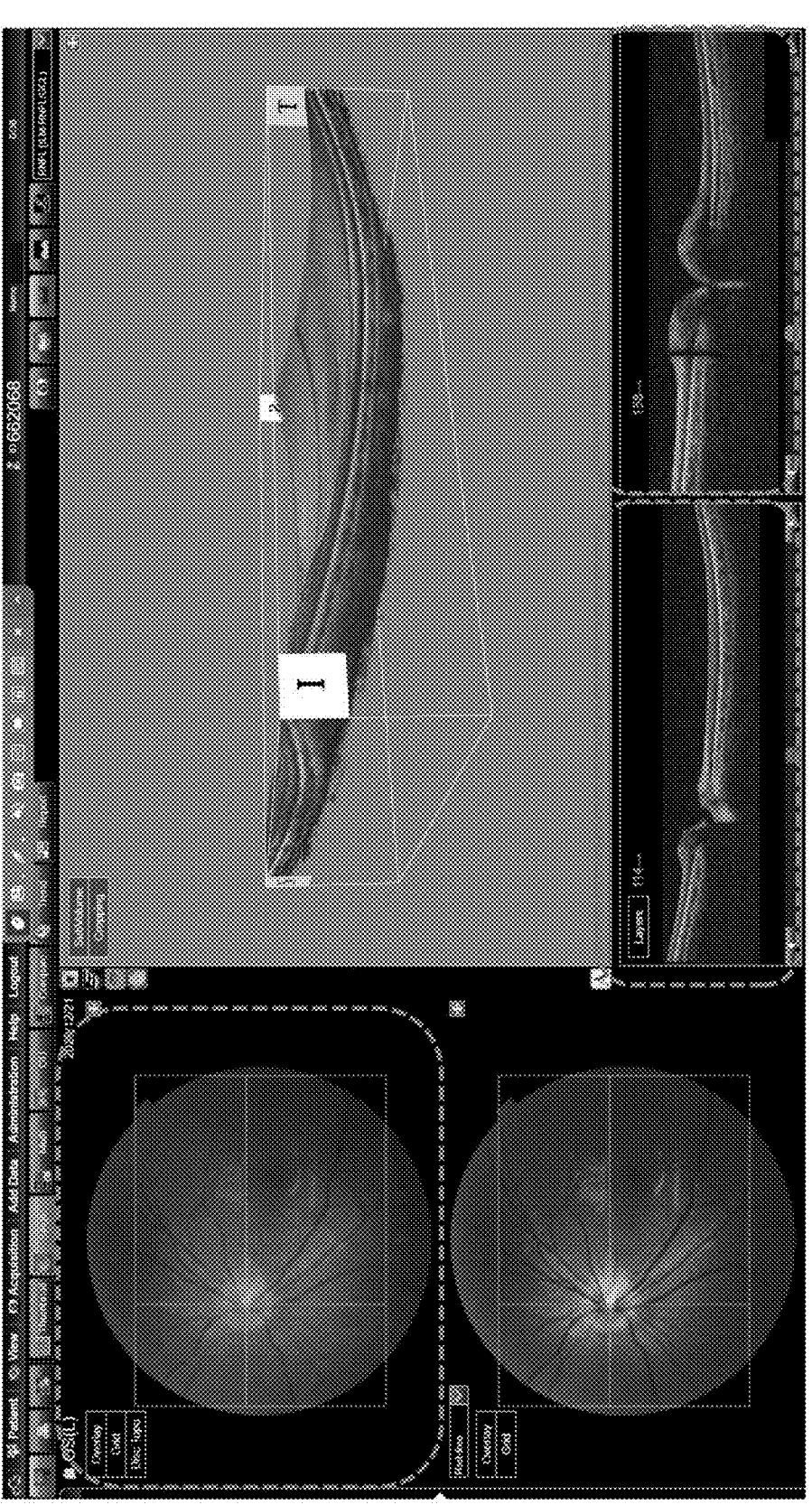

FIG. 10 is a diagram showing the OCT cross-sectional image of an eyeball taken along the center line of the OCT cross-sectional image of an eyeball in FIG. 9.

Figure 11:
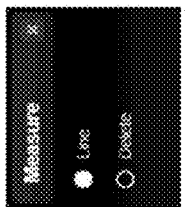
Figure 11:

FIG. 11 is a diagram showing the OCT cross-sectional image of an eyeball taken along the center line in FIG. 9.

Figure 12:
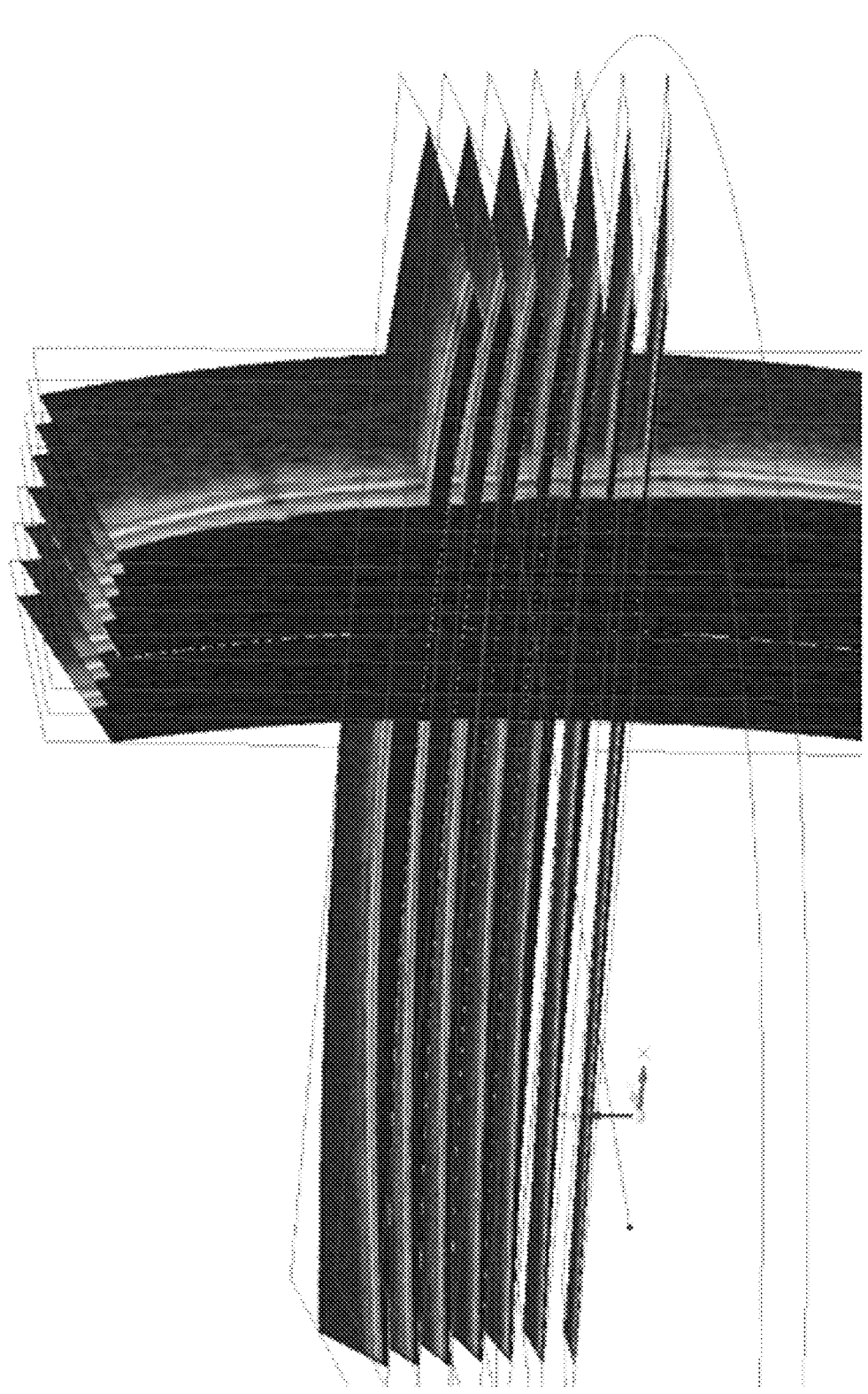

FIG. 12 is a diagram showing the production of a high-resolution model in an OCT observation area by stacking the OCT cross-sectional images of an eyeball in an MRI coordinate system.

Figure 13:
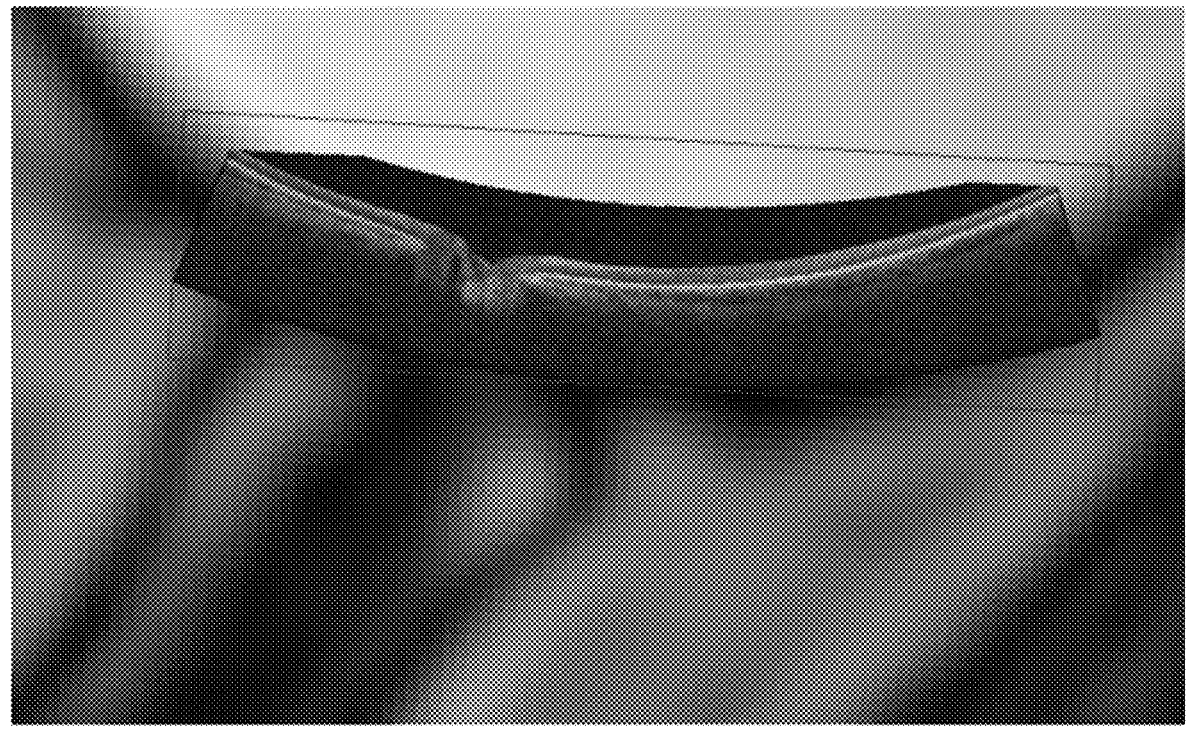

FIG. 13 is a diagram showing an example of a high-resolution form captured by OCT in an OCT observation area.

Figure 14:
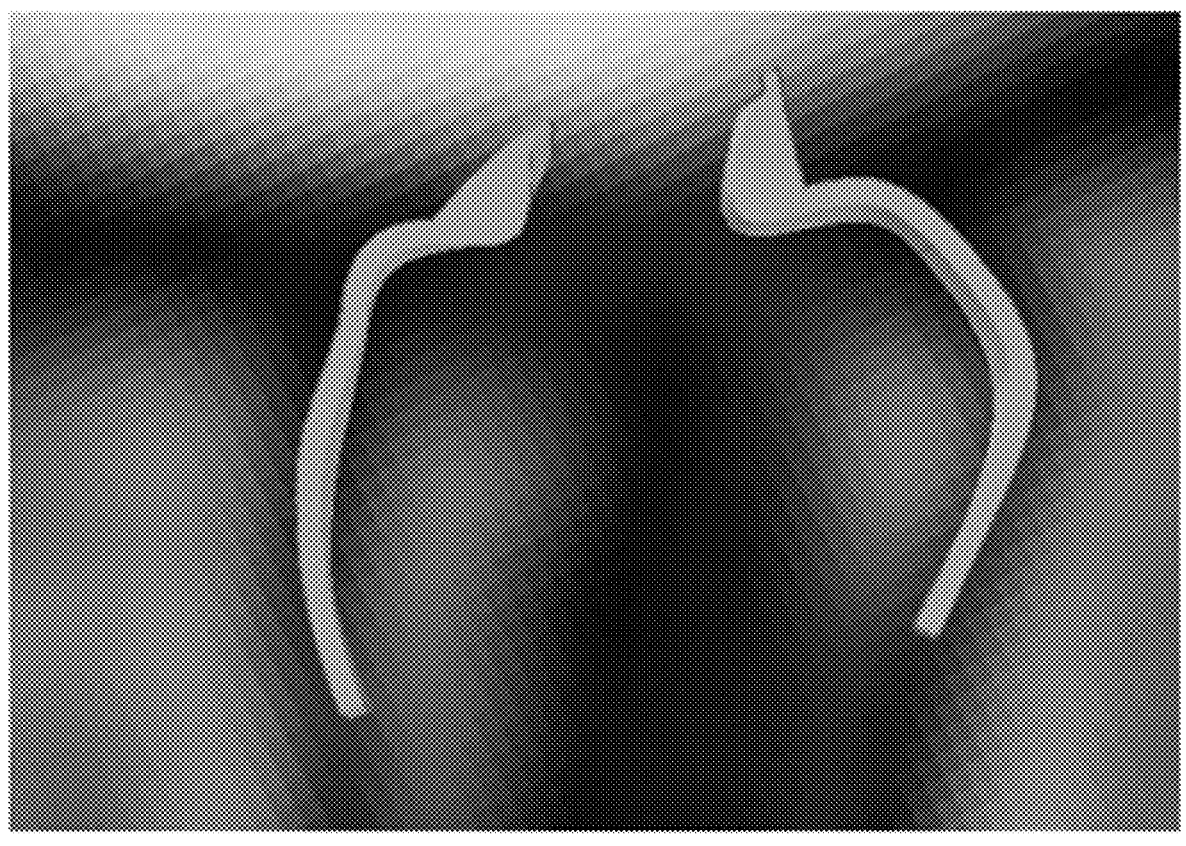

FIG. 14 is a diagram showing modeling of an OCT dark area using MRI.

Figure 15:
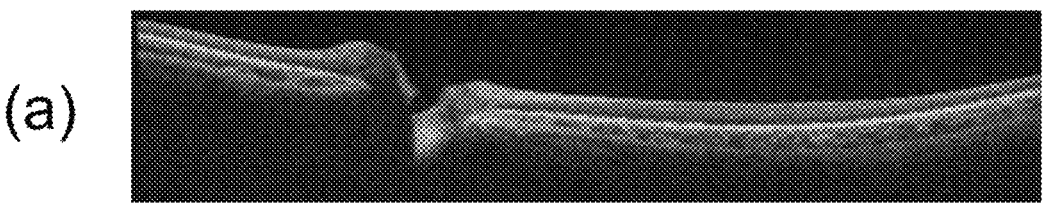
Figure 15:
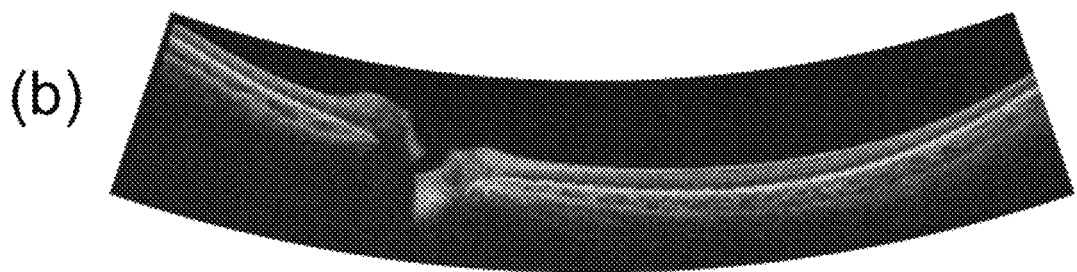
Figure 15:
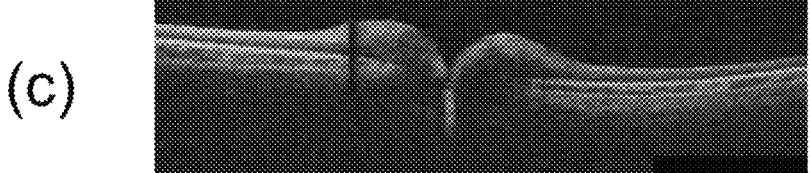
Figure 15:
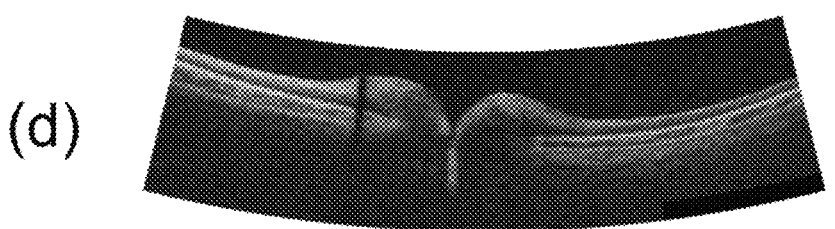

(a), (b), (c), and (d) of FIG. 15 are diagrams showing the process of correcting distortion of the OCT cross-sectional images of an eyeball.

Figure 16:
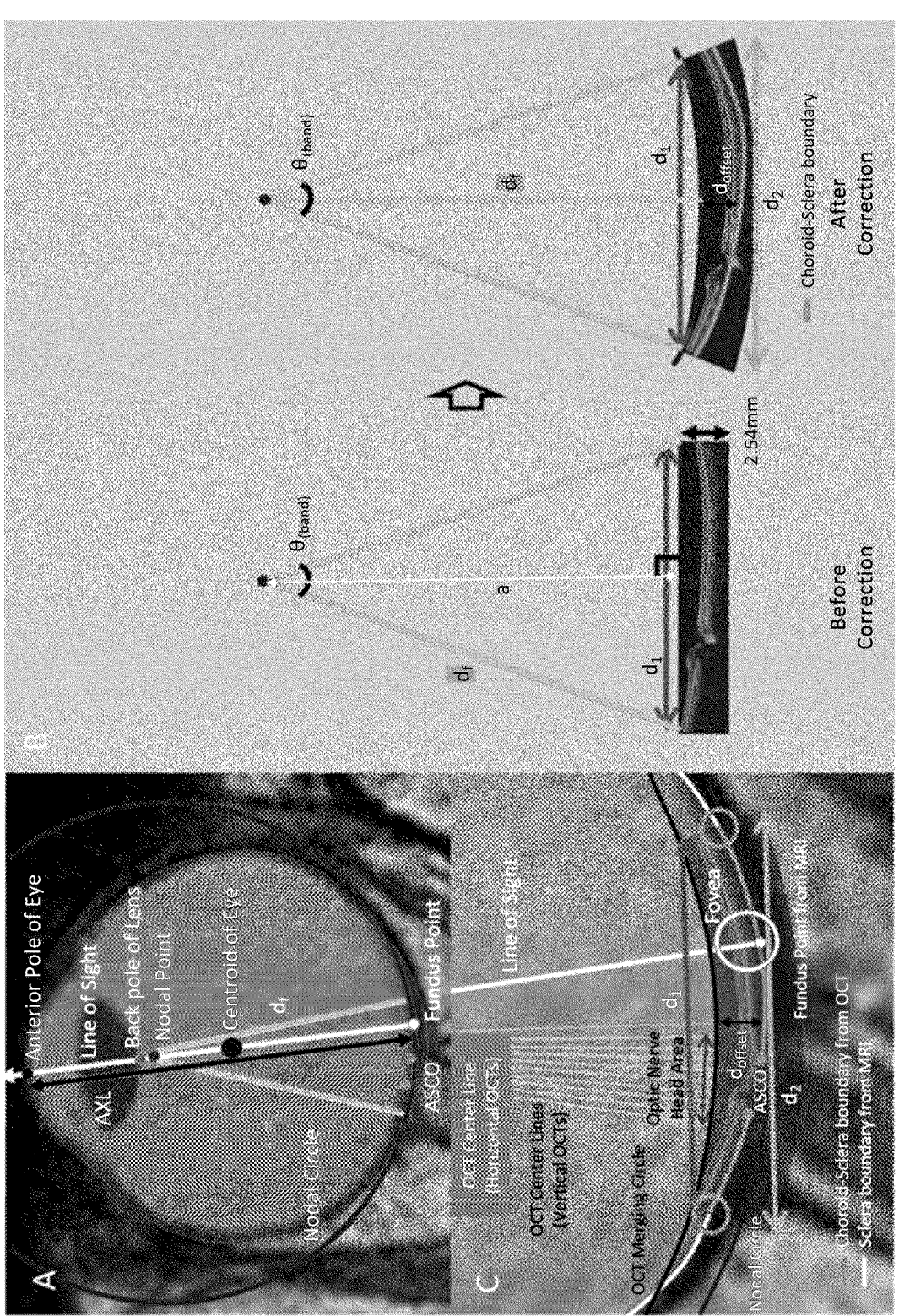

(A), (B), and (C) of FIG. 16 are diagrams showing the process of arranging and aligning the OCT cross-sectional image of an eyeball in the process of correcting distortion of the OCT cross-sectional image of an eyeball.

Figure 17:
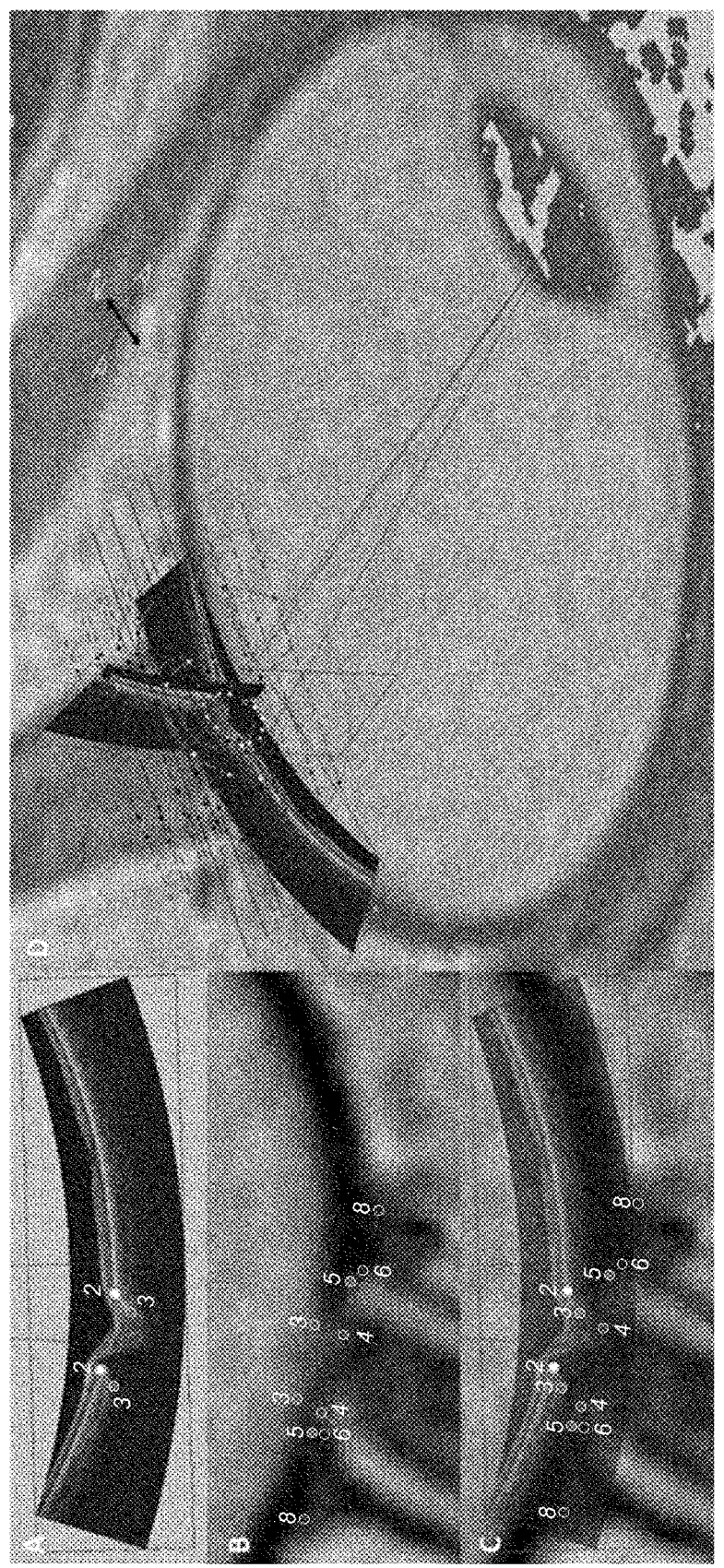

(A), (B), (C), and (D) of FIG. 17 are diagrams showing points used in modeling in the process of correcting distortion of the OCT cross-sectional images of an eyeball.

Figure 18:
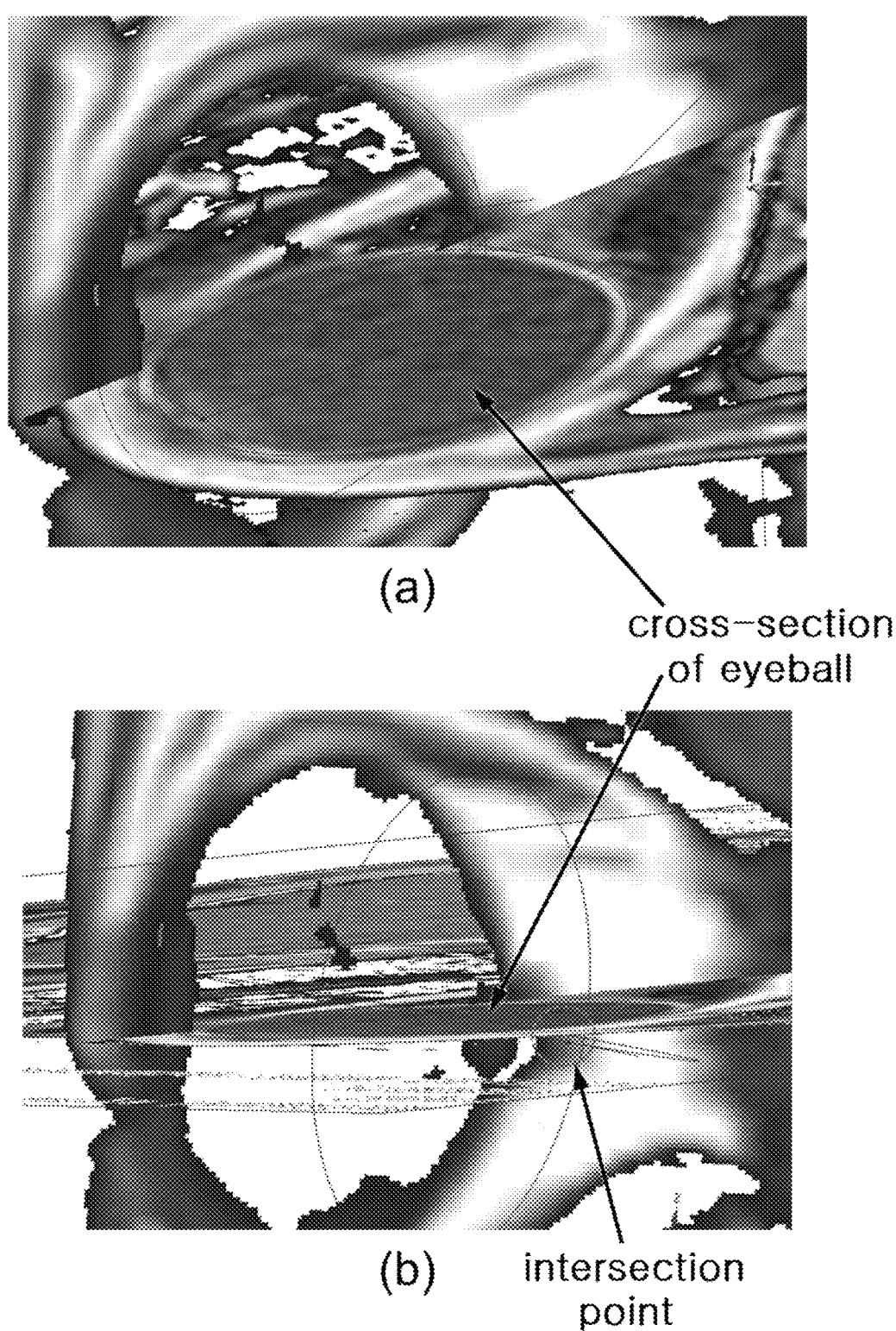

(a) and (b) of FIG. 18 are diagrams showing forming an inscribed circle and intersection point of an eyeball in an MRI head image with a larger eyeball among first and second MRI head images.

Figure 19:

FIG. 19 is a diagram showing the process of obtaining an intersection point for merging corrected OCT cross-sectional images of an eyeball.

Figure 20:
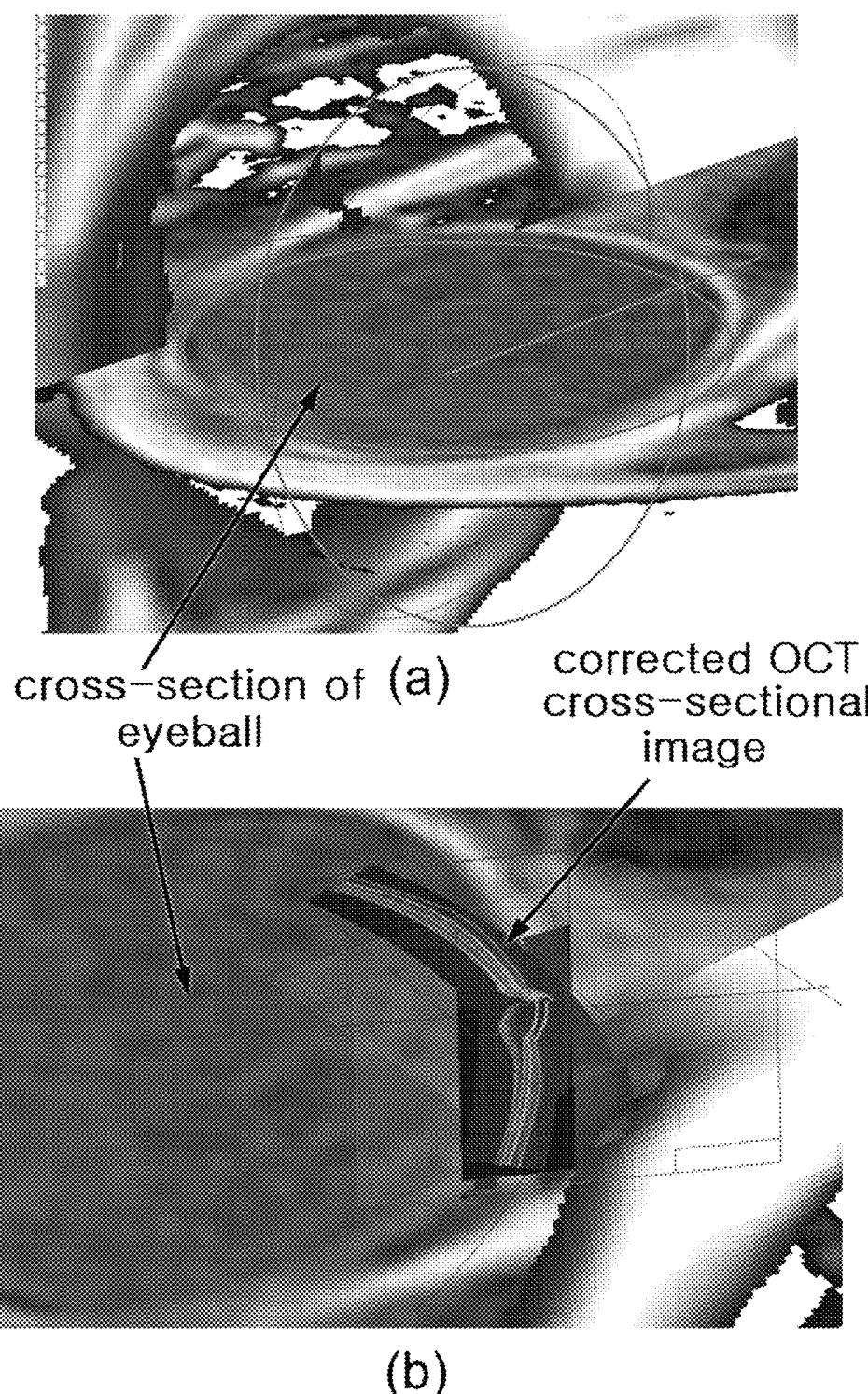

(a) and (b) of FIG. 20 are diagrams showing obtaining an intersection point from a MRI head image with a larger eyeball among first and second MRI head images and then merging the corrected OCT cross-sectional images of an eyeball to the obtained intersection point.

Figure 21:
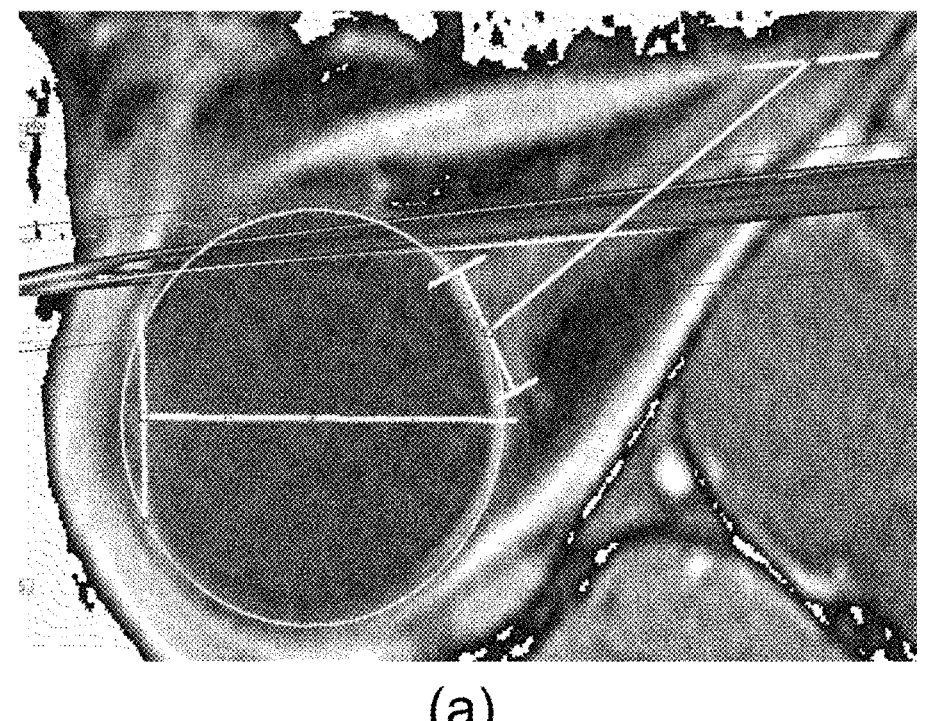
Figure 21:
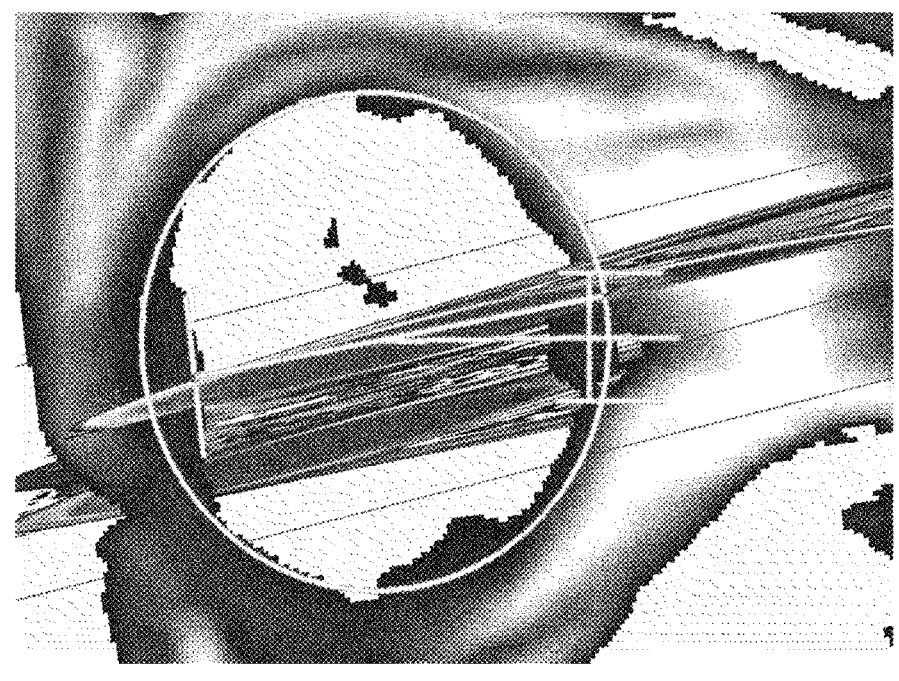

(a) of FIG. 21 is a diagram showing obtaining the coordinates of the matched part of the center point of the optic nerve and the optic disk.

(b) of FIG. 21 is a diagram showing the process of merging the corrected OCT cross-sectional images of an eyeball.

Figure 22:
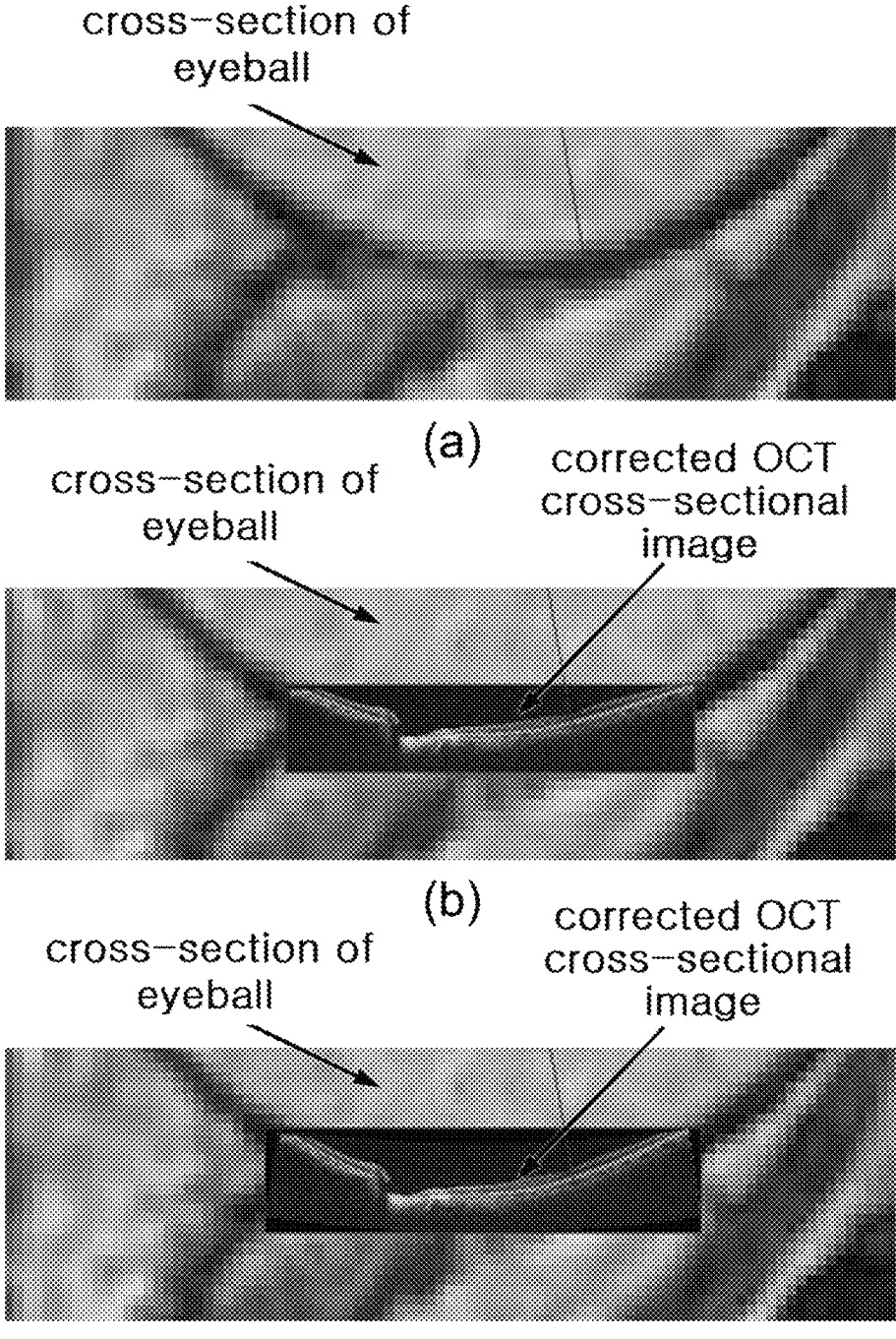

(a), (b), and (c) of FIG. 22 are diagrams showing the process of merging the corrected OCT cross-sectional image of an eyeball with an MRI head image.

Figure 23:
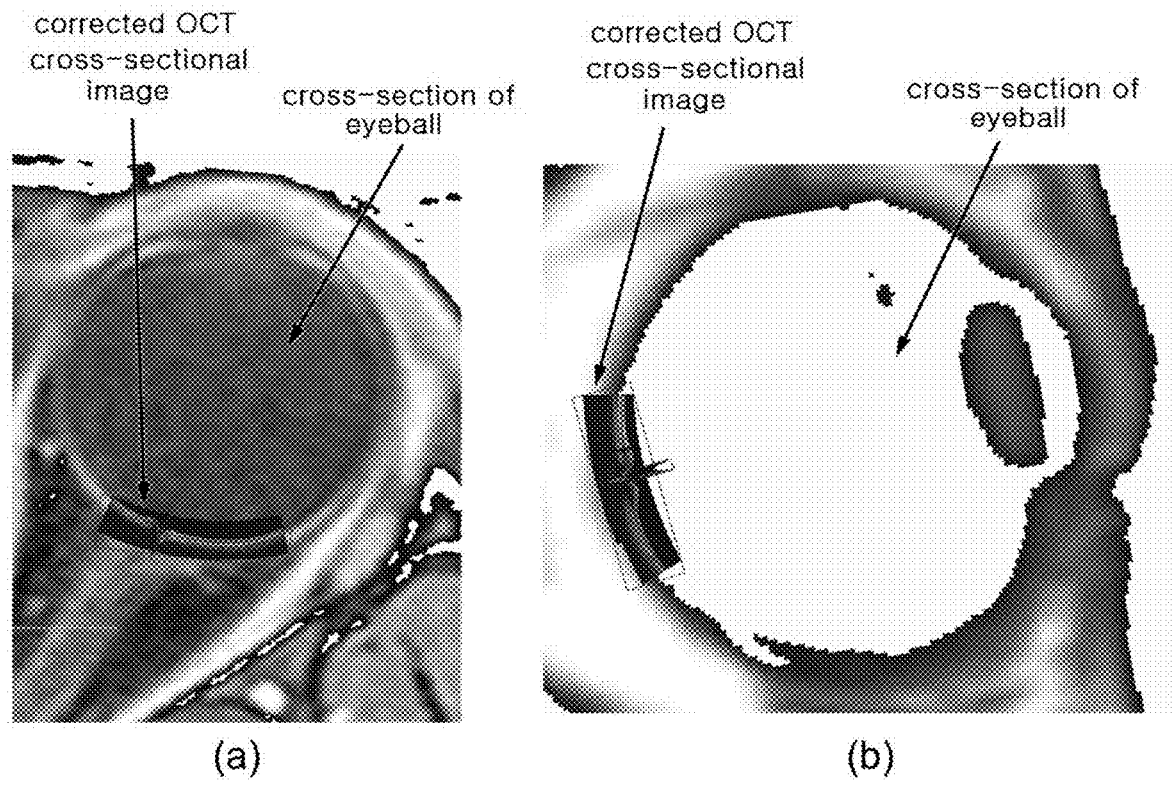

(a) and (b) of FIG. 23 are diagrams showing matching the corrected OCT cross-sectional image of an eyeball onto an MRI head image with a larger eyeball among first and second MRI head images.

Figure 24:
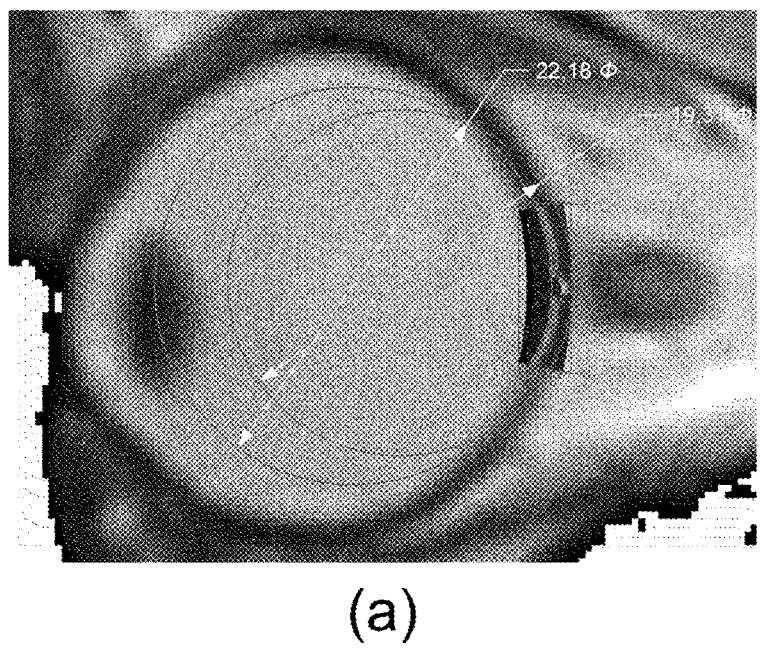
Figure 24:
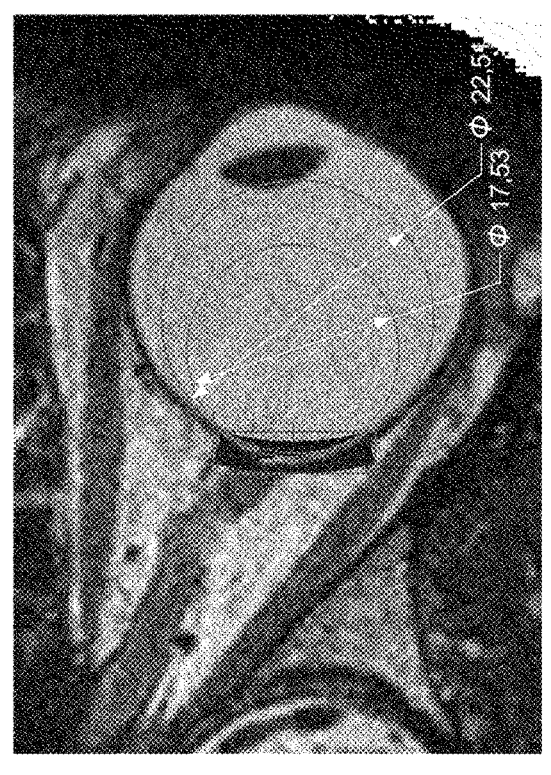

(a) and (b) of FIG. 24 are diagrams showing the formation of a plurality of inscribed circles in an MRI head image with a larger eyeball among first and second MRI head images.

Figure 25:
Figure 25:
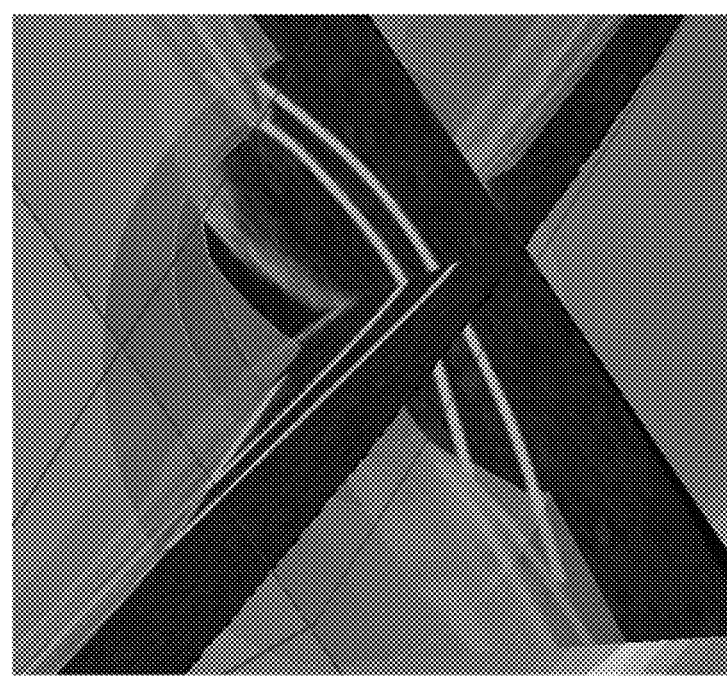

(a) and (b) of FIG. 25 are diagrams showing the process of forming an ASCO on a corrected OCT cross-sectional image of an eyeball.

Figure 26:
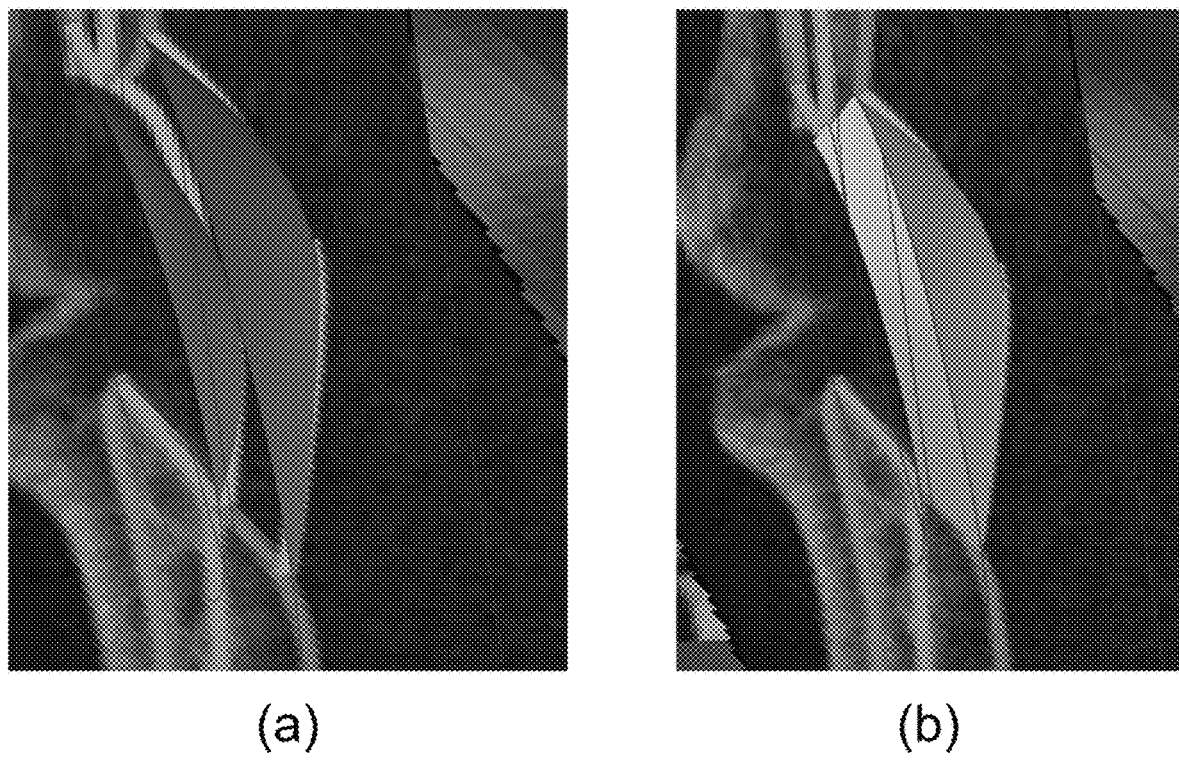

(a) and (b) of FIG. 26 are diagrams showing the process of forming a lamina cribrosa on a corrected OCT cross-sectional image of an eyeball.

Figure 27:
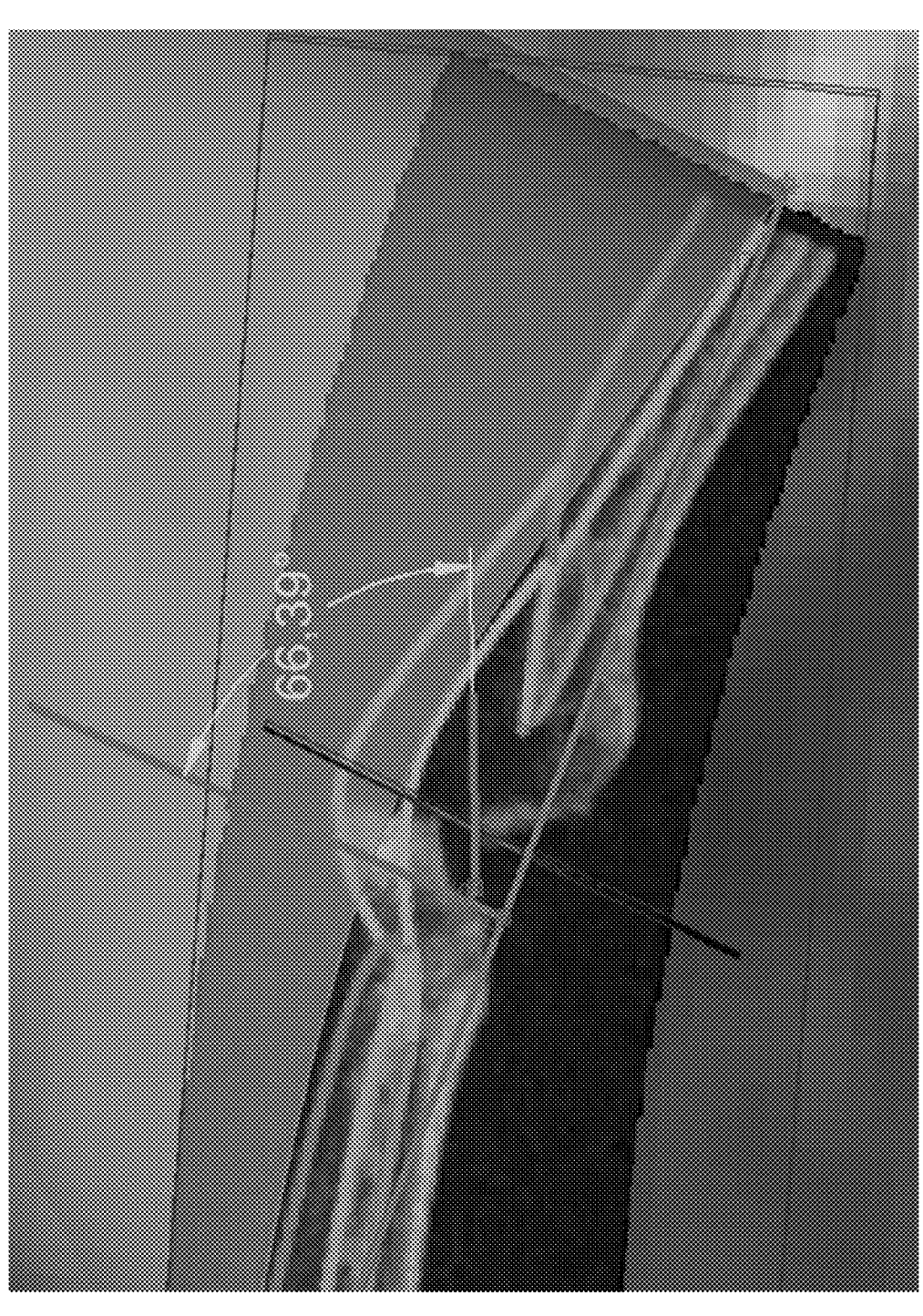

FIG. 27 is a diagram showing the included angle in the image shown in FIG. 22(Aa).

Figure 28:
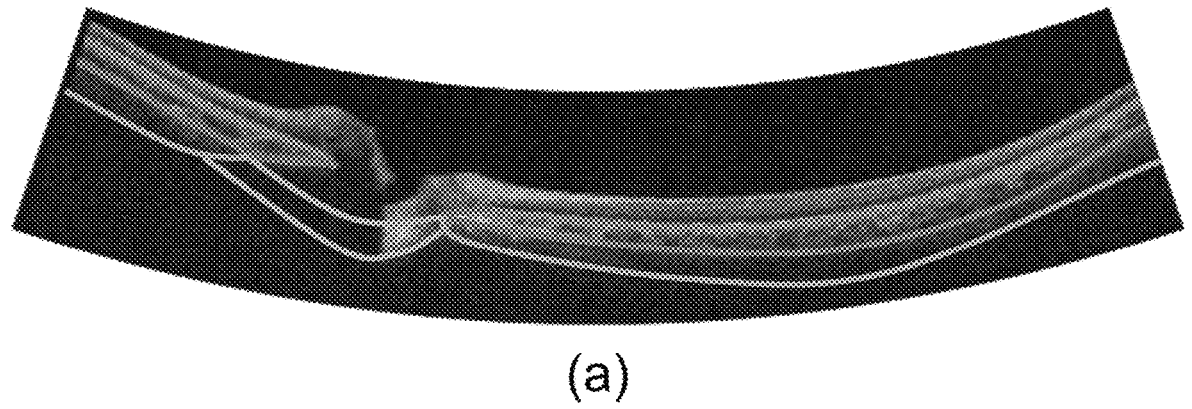
Figure 28:
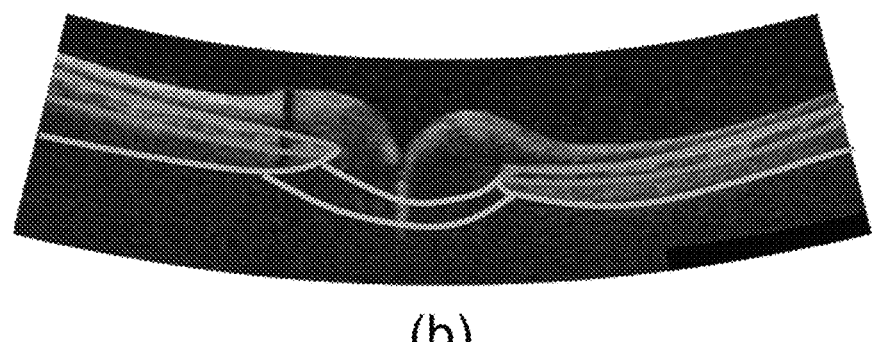

FIG. 28 is a diagram showing the formation of BMO, choroid opening, and ASCO in a corrected OCT cross-sectional image of an eyeball.

Figure 29:
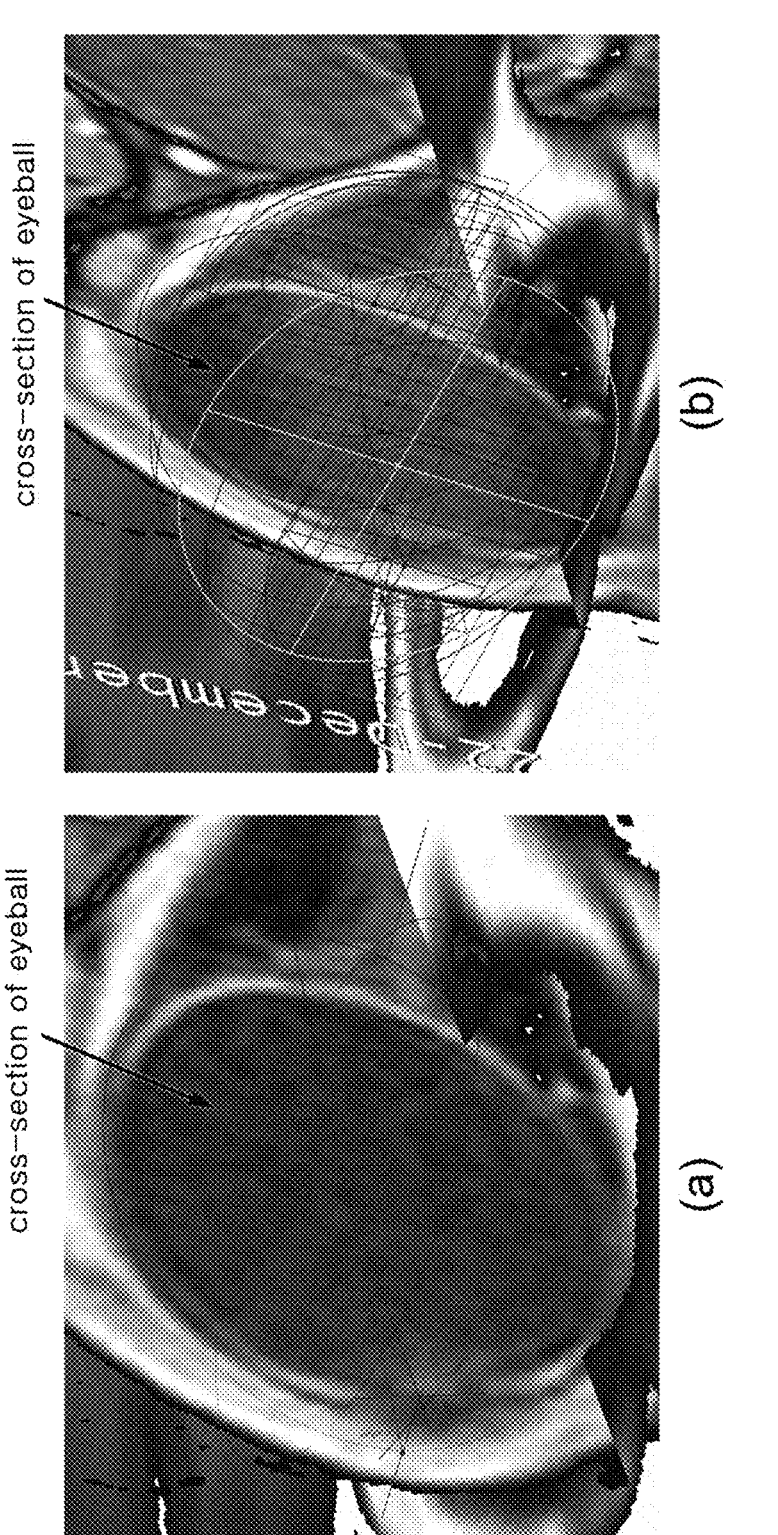
Figure 30:
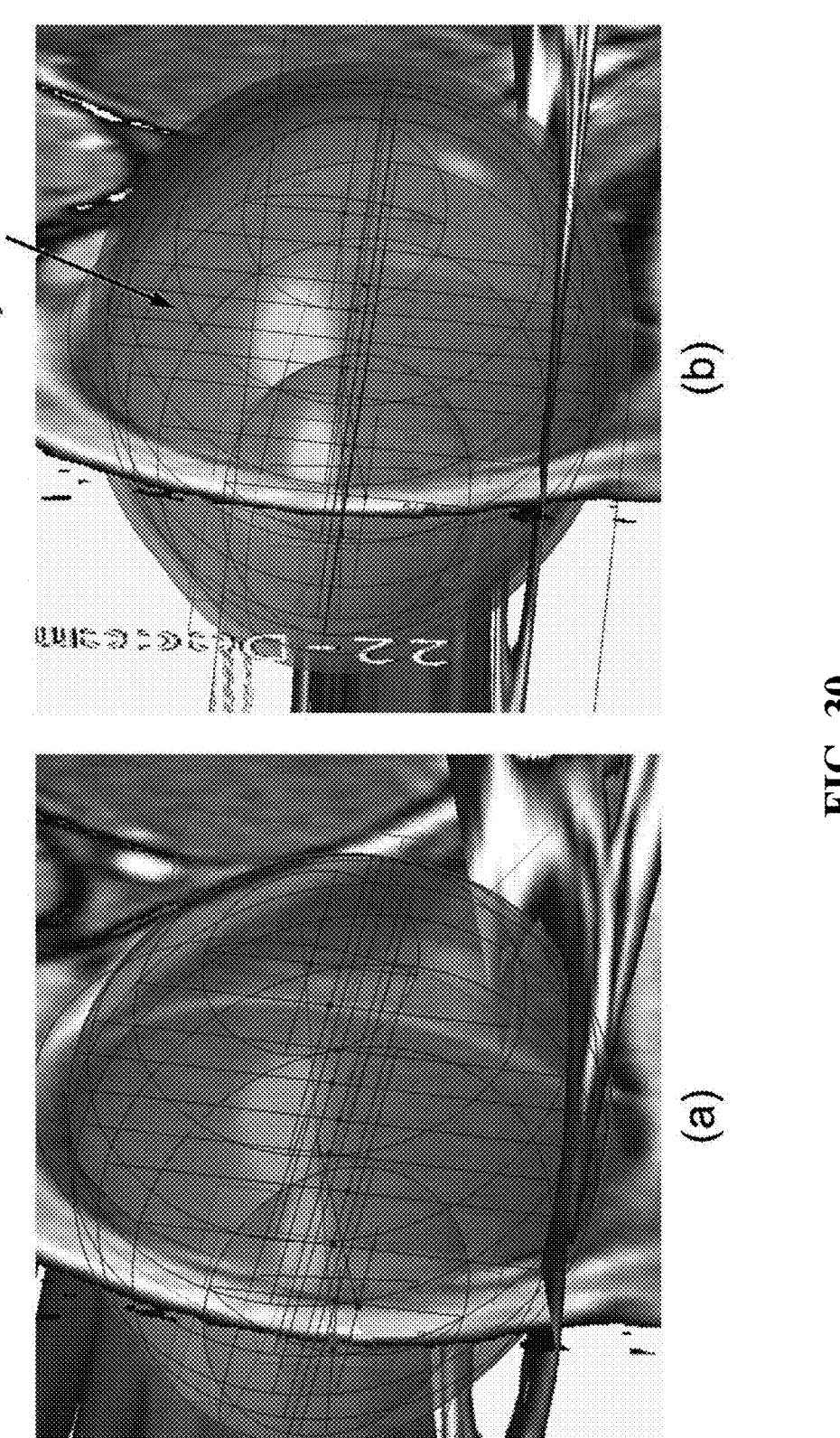

FIGS. 29 and 30 are diagrams showing three-dimensional modeling of an eyeball model in an MRI head image with a larger eyeball among first and second MRI head images.

Figure 31:
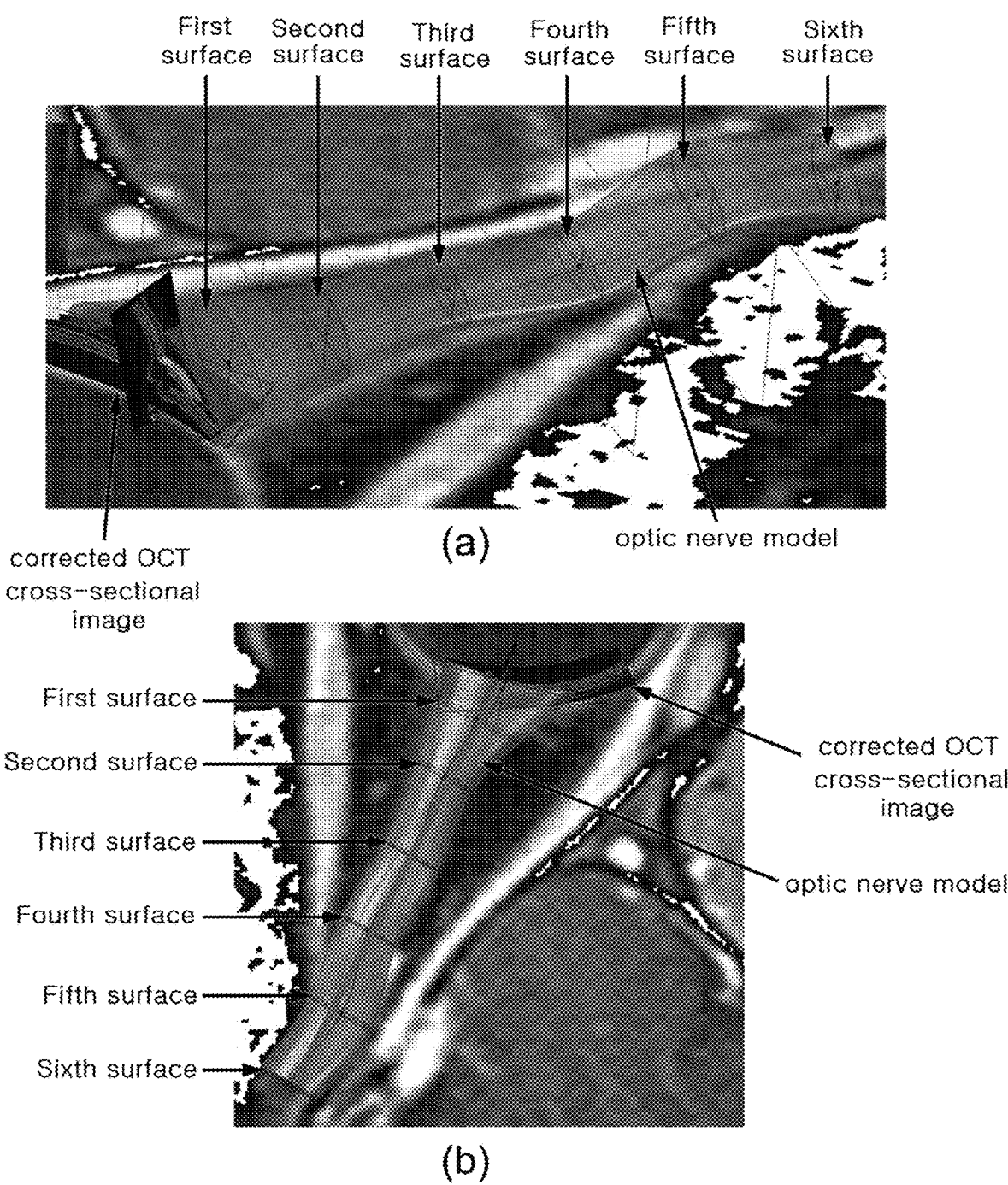

(a) and (b) of FIG. 31 are diagrams showing the process of three-dimensionally modeling an optic nerve model.

Figure 32:
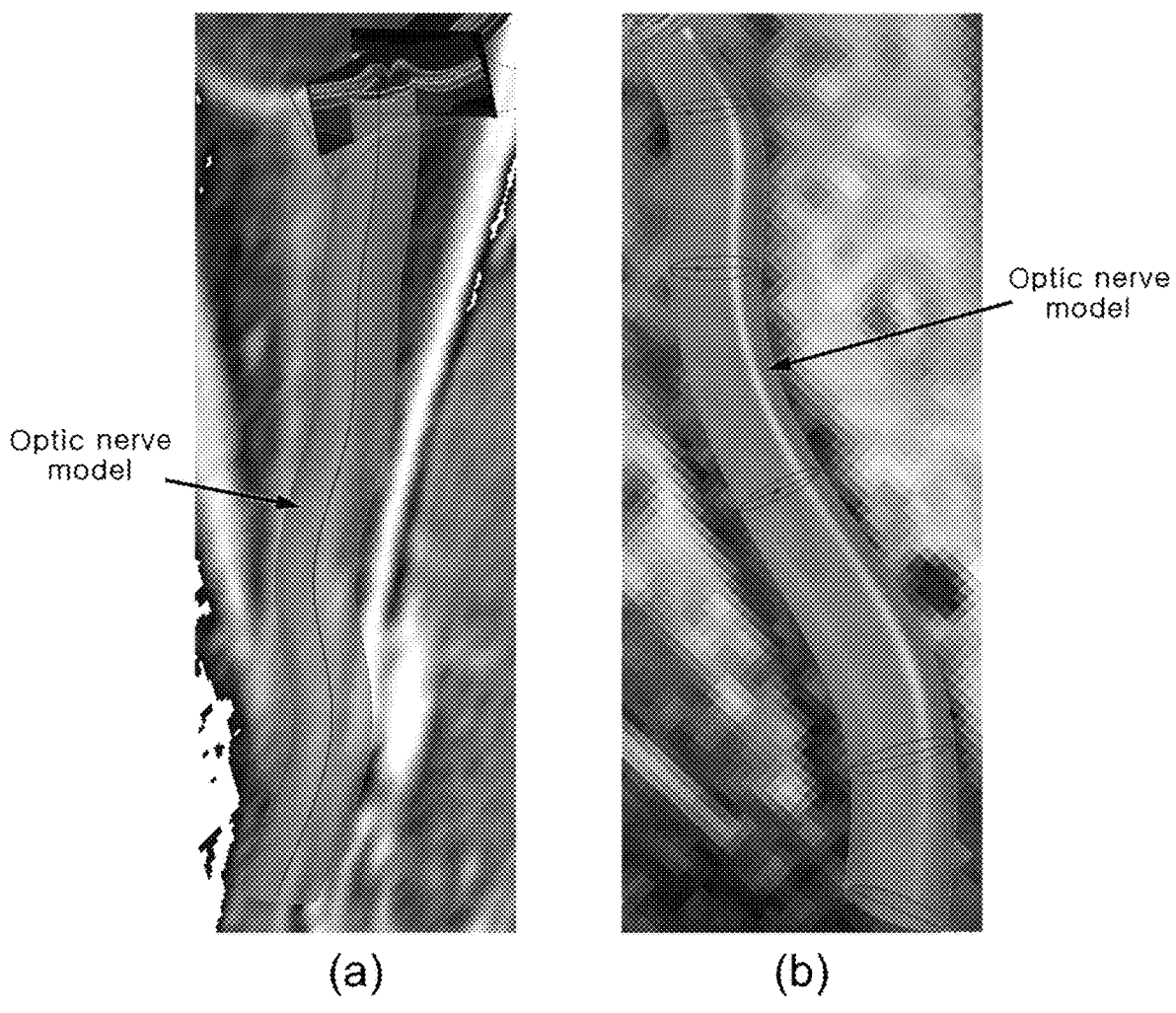

(a) and (b) of FIG. 32 are diagrams showing a three-dimensionally modeled optic nerve model.

Figure 33:
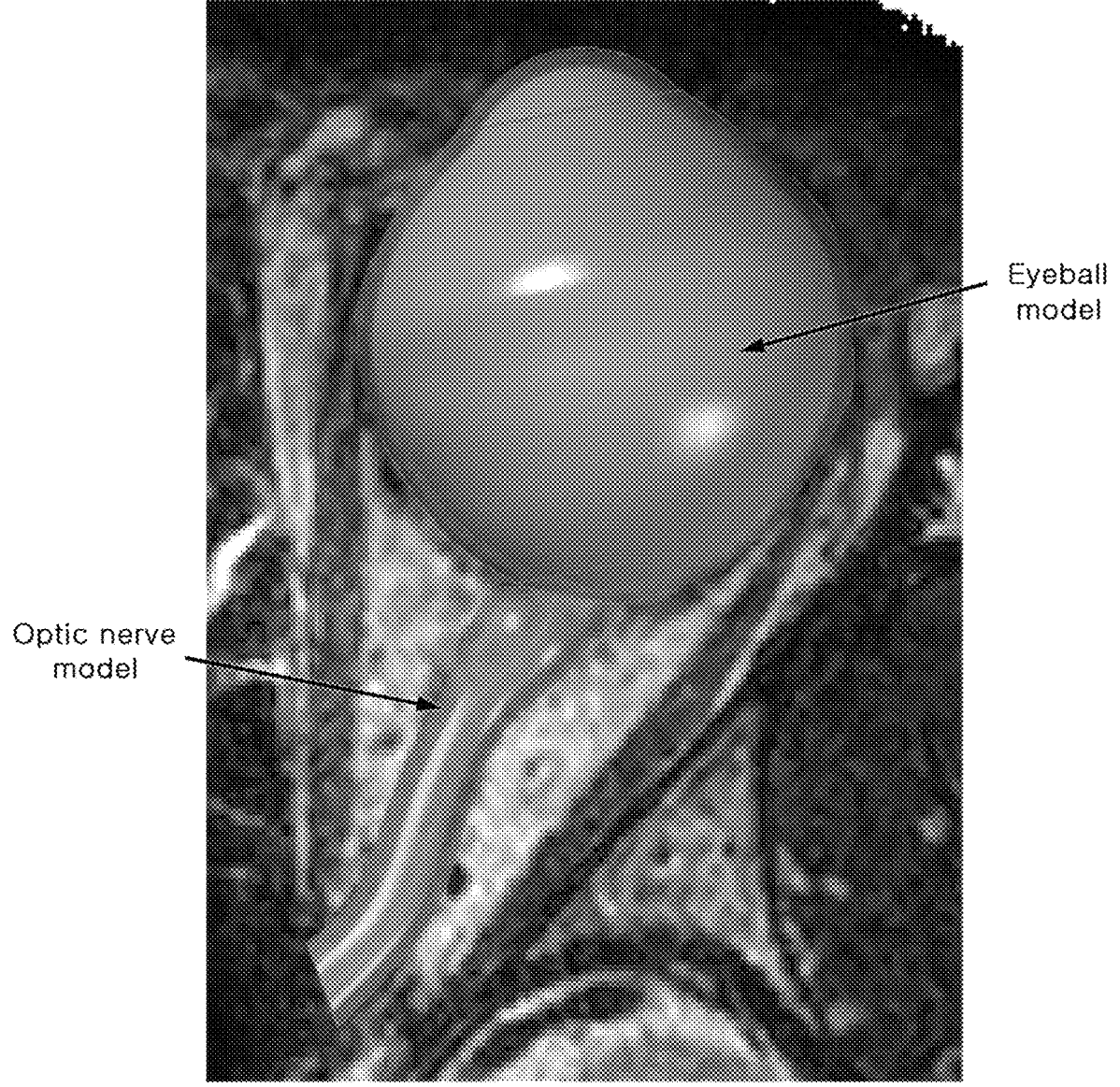

FIG. 33 is a diagram showing an eyeball model and an optic nerve model.

Figure 34:
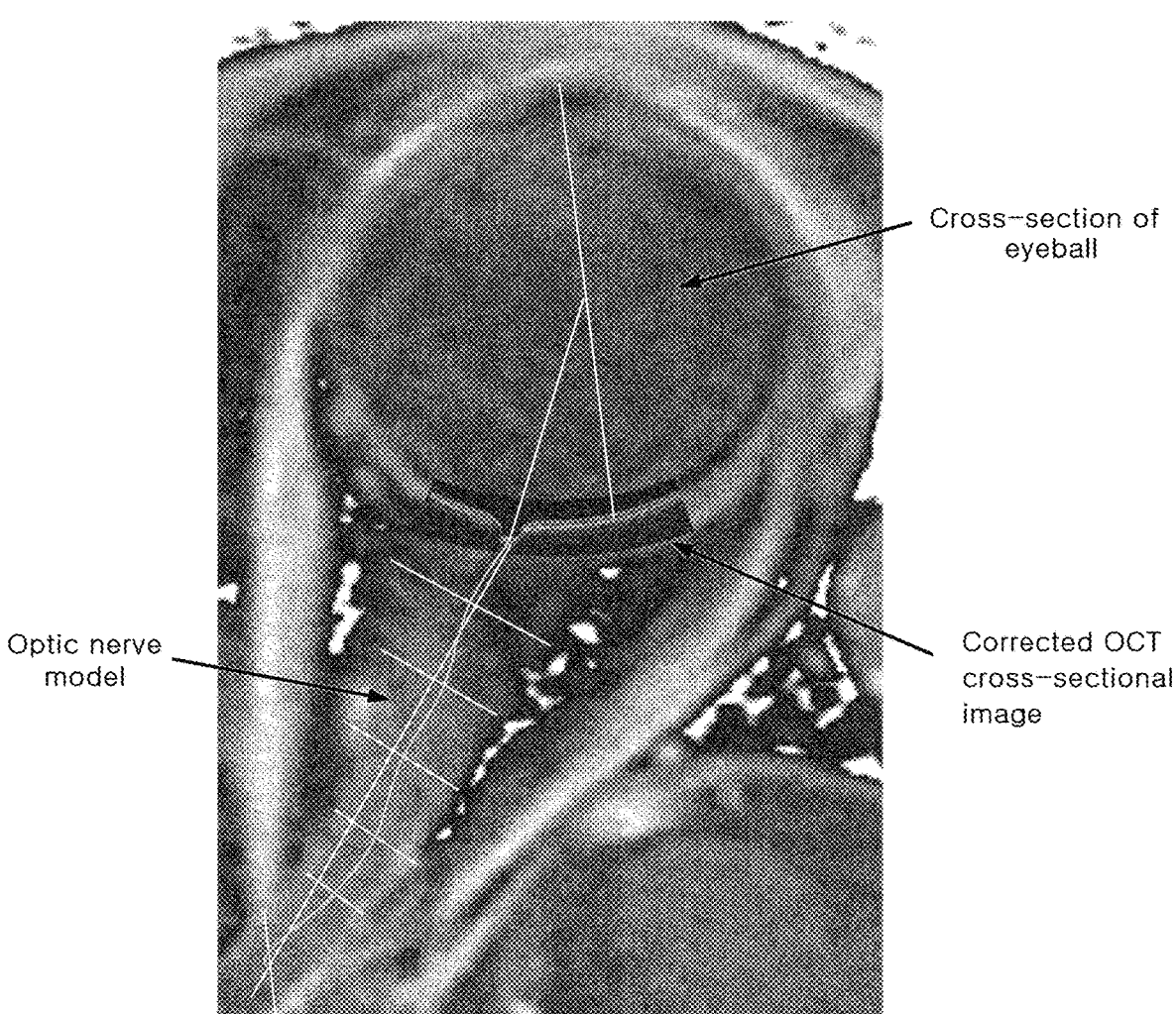

FIG. 34 is a diagram showing measurement of the axial length, straight line distance from the center of the filiform plate to the optic nerve root, left and right widths dividing the straight line distance into five equal parts, ratio of the straight line distance to the cochlear width, curve connecting the centers of the left and right widths, and length of the curve in a state where the corrected OCT cross-sectional image of an eyeball is matched onto the MRI head image with a larger eyeball among first and second MRI head images.

Figure 35:
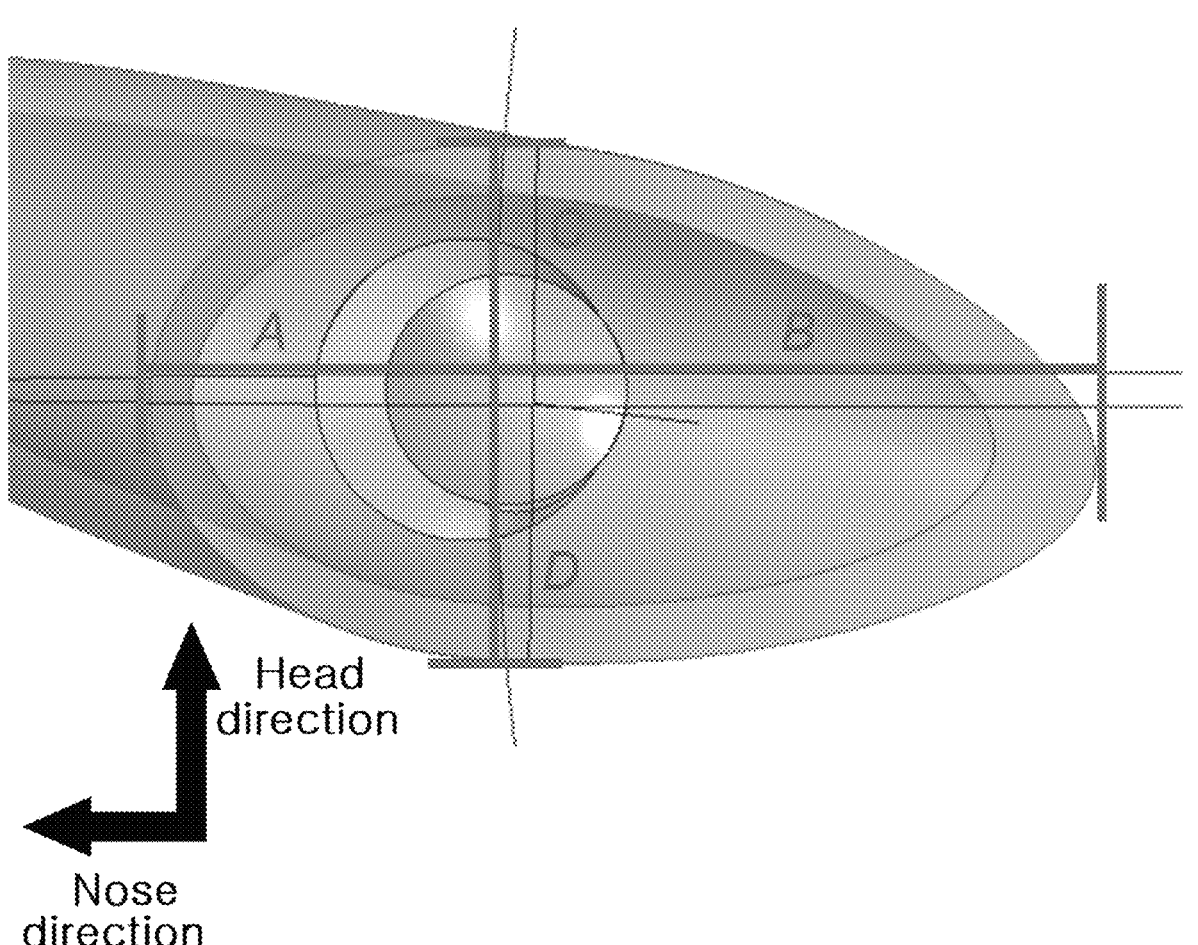

FIG. 35 is a cross-sectional perspective view showing an optic nerve model.

Figure 36:
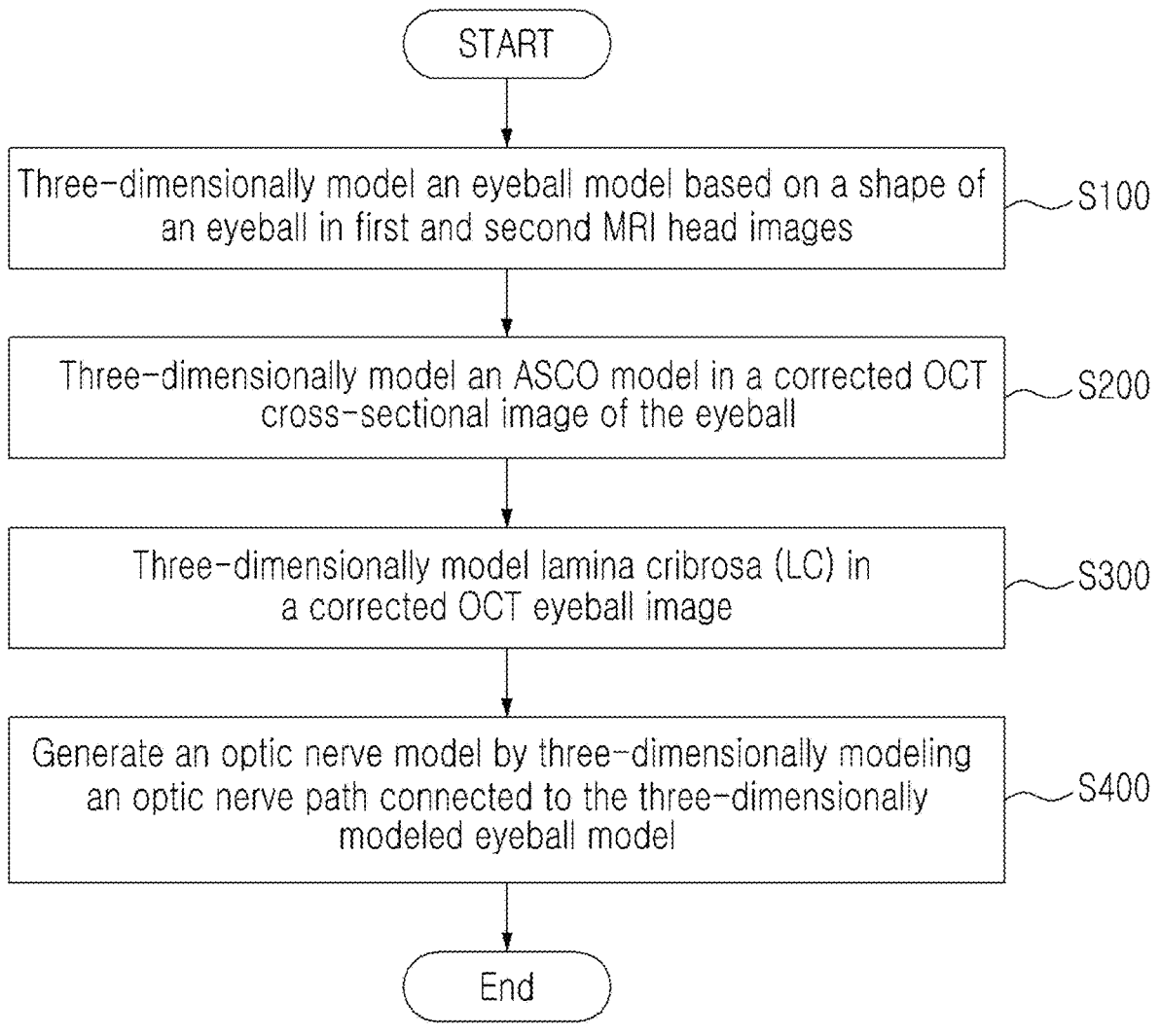

FIG. 36 is a flowchart showing a method for three-dimensionally modeling an eyeball and an optic nerve using a merge of an MRI image and an OCT image according to an embodiment of the present invention.

BEST MODE

A preferred embodiment of the present invention comprises the steps of (a) three-dimensionally modeling an eyeball model based on a shape of an eyeball in first and second MRI head images; (b) three-dimensionally modeling an ASCO model in a corrected OCT cross-sectional image of the eyeball; (c) three-dimensionally modeling lamina cribrosa (LC) in a corrected OCT eyeball image; and (d) generating an optic nerve model by three-dimensionally modeling an optic nerve path connected to the three-dimensionally modeled eyeball model. The first MRI head image is an MRI head image with the largest eyeball among a plurality of the first MRI head images, each image being sliced in the XY plane, and the second MRI head image is an MRI head image with the largest eyeball among a plurality of the second MRI head images, each image being sliced in the XZ plane.

MODE FOR INVENTION

Hereinafter, the present invention will be explained with reference to the accompanying drawings. The present invention, however, may be modified in various different ways, and should not be construed as limited to the embodiments set forth herein. Also, in order to clearly explain the present invention, portions that are not related to the present invention are omitted, and like reference numerals are used to refer to like elements throughout.

Throughout the specification, it will be understood that when an element is referred to as being "connected (accessed, contacted, coupled) to" another element, it may be "directly connected to" the other element, or intervening elements may be present. Also, it will also be understood that when a component "includes" an element, unless stated otherwise, it should be understood that the element does not exclude other elements.

Terms used in the present specification are used only to describe specific exemplary embodiments, and are not intended to limit the present invention. A singular form may include a plural form if there is no clearly opposite meaning in the context. In this specification, it should be understood that the term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

Hereinafter, an embodiment of the present invention will be described in more detail with reference to the accompanying drawings.

1. Generation Method of an Optic Nerve Path Using a Match of an MRI Image and an OCT Image Hereinafter, a method for generating an optic nerve path using a match of an MRI image and an OCT image according to an embodiment of the present invention will be described with reference to FIGS. 1 to 33.

Figure 1:
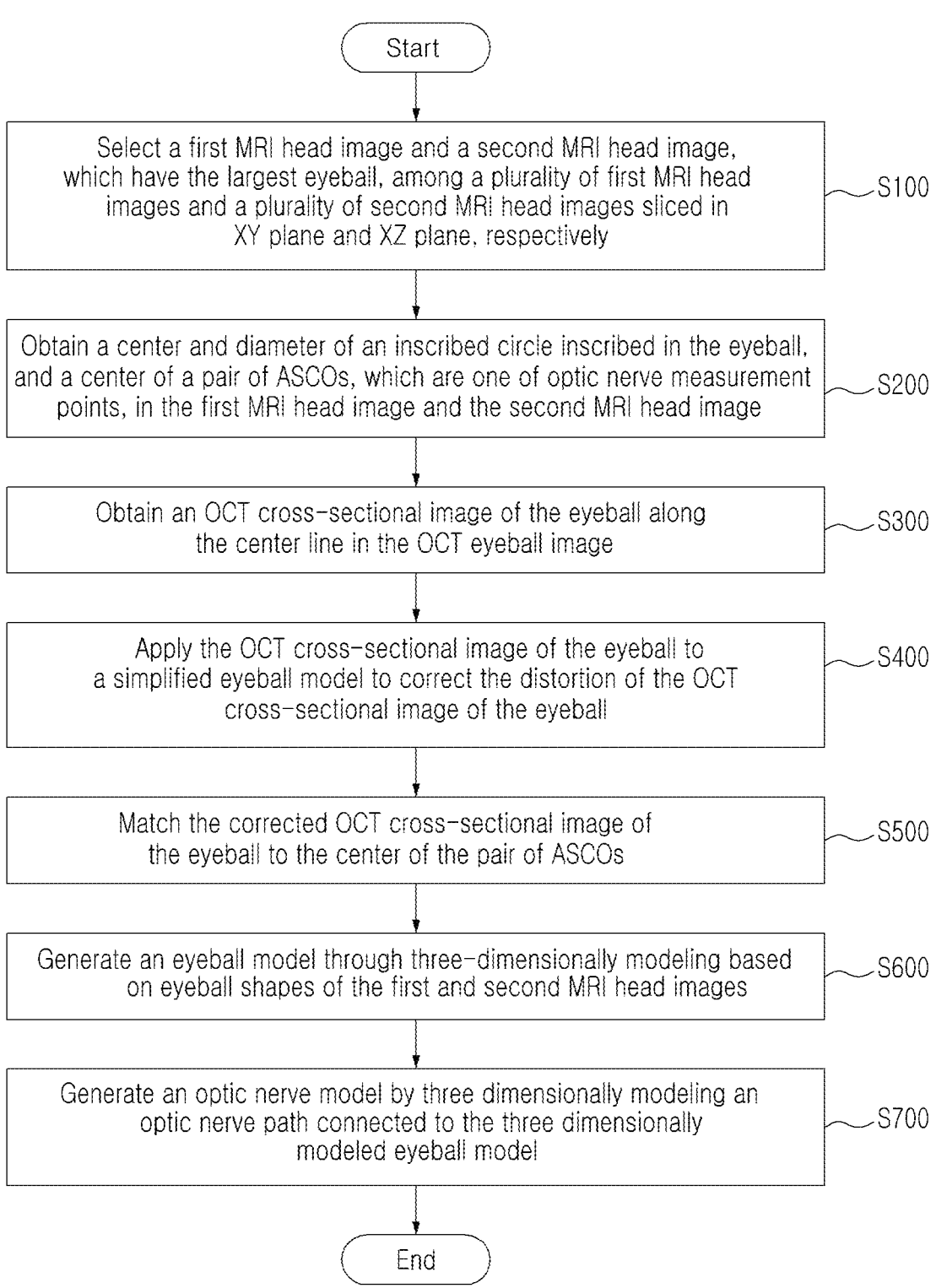
FIG. 1 is a flowchart showing a method for generating an optic nerve path using a match of an MRI image and an OCT image according to an embodiment of the present invention.

FIG. 1 is a flowchart showing a method for generating an optic nerve path using a match of an MRI image and an OCT image according to an embodiment of the present invention.

Referring to FIG. 1, a method for generating an optic nerve path using a match of an MRI image and an OCT image according to an embodiment of the present invention comprises the steps of (a) selecting a first MRI head image and a second MRI head image, which have the largest eyeball, among a plurality of first MRI head images and a plurality of second MRI head images, the first MRI head images and the second MRI head images being sliced in the XY plane and XZ plane, respectively (S100), (b) obtaining a center and diameter of an inscribed circle inscribed in the eyeball, and a center of a pair of ASCOs, which are one of optic nerve measurement points, in the first MRI head image and the second MRI head image (S200), (c) obtaining an OCT cross-sectional image of the eyeball along the center line in the OCT eyeball image (S300), (d) applying the OCT cross-sectional image of the eyeball to a simplified eyeball model to correct the distortion of the OCT cross-sectional image of the eyeball (S400), (e) matching the corrected OCT cross-sectional image of the eyeball to the center of the pair of ASCOs (S500), (f) generating an eyeball model through three-dimensionally modeling based on the eyeball shapes of the first and second MRI head images (S600), and (g) generating an optic nerve model by three dimensionally modeling an optic nerve path connected to the three dimensionally modeled eyeball model (S700).

Figure 2:
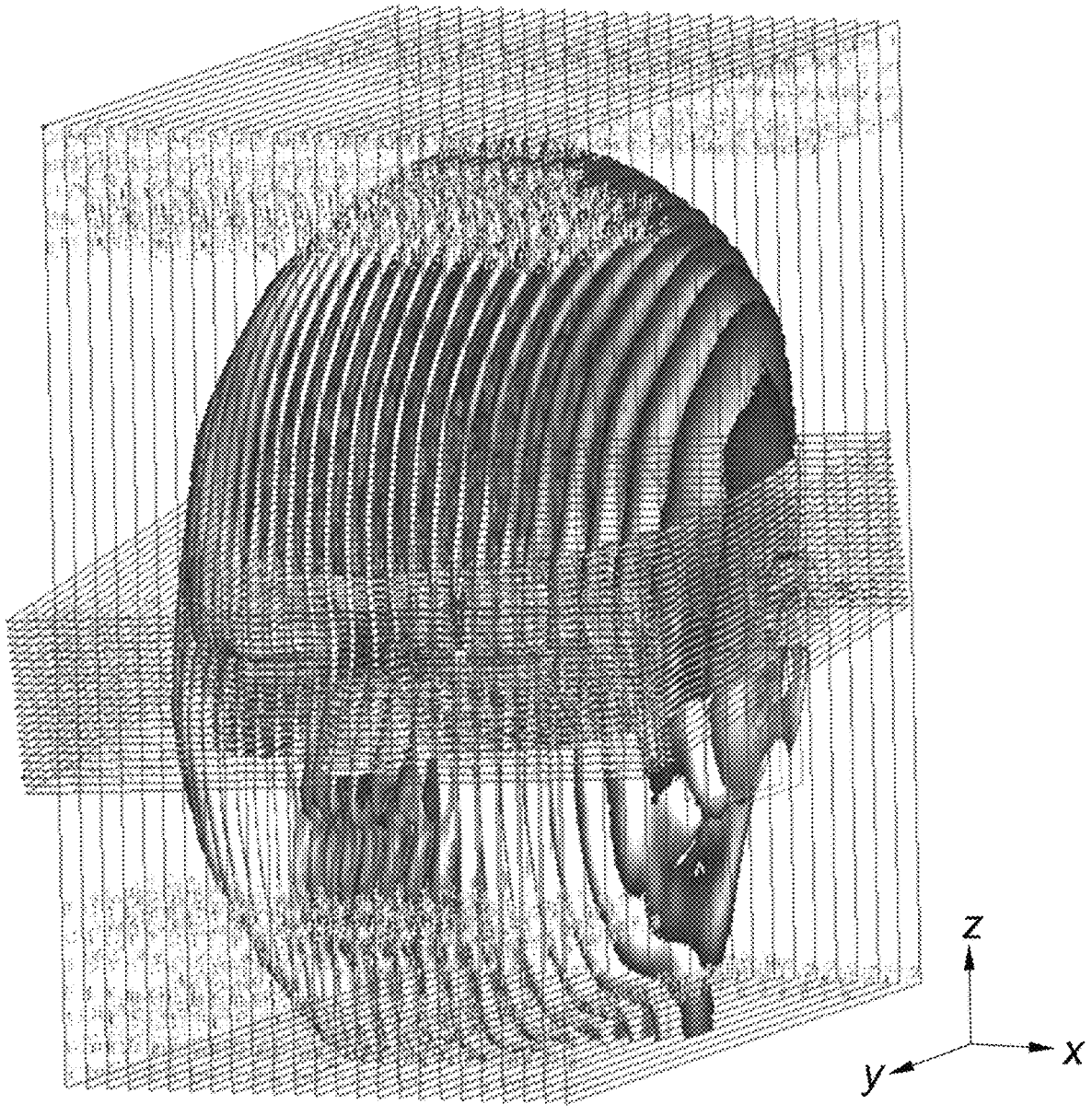
FIG. 2 is a diagram showing a plurality of MRI head images sliced in the XY plane and XZ plane in a three-dimensional space.

FIG. 2 is a diagram showing a plurality of MRI head images sliced in the XY plane and XZ plane in a three-dimensional space.

The step (a) comprises the steps of (a1) obtaining the plurality of first MRI head images sliced into the XY plane by capturing the head, (a2) obtaining the plurality of second MRI head images sliced into the XZ plane by capturing the head, (a3) selecting the first MRI head image having the largest eyeball from the plurality of first MRI head images, (a4) selecting the second MRI head image having the largest eyeball from the plurality of second MRI head images.

In this case, the plurality of first MRI head images and the plurality of second MRI head images are images captured to necessarily include the eyeball.

Referring to FIG. 2, in steps (a1) and (a2), a magnetic resonance imaging (MRI) device images the patient's head and obtains the plurality of first MRI head images sliced in the XY plane and the plurality of second MRI head images sliced in the XZ plane.

For example, the number of the plurality of first MRI head images sliced in the XY plane may be 23, and the number of the plurality of second MRI head images sliced in the XZ plane may be 25, but the numbers are not limited thereto.

In addition, the plurality of first MRI head images sliced in the XY plane and the plurality of second MRI head images sliced in the XZ plane are the images implemented in a three-dimensional space through a three-dimension modeling program using multiple MRI Dicoms, as shown in FIG. 2.

Figure 3:
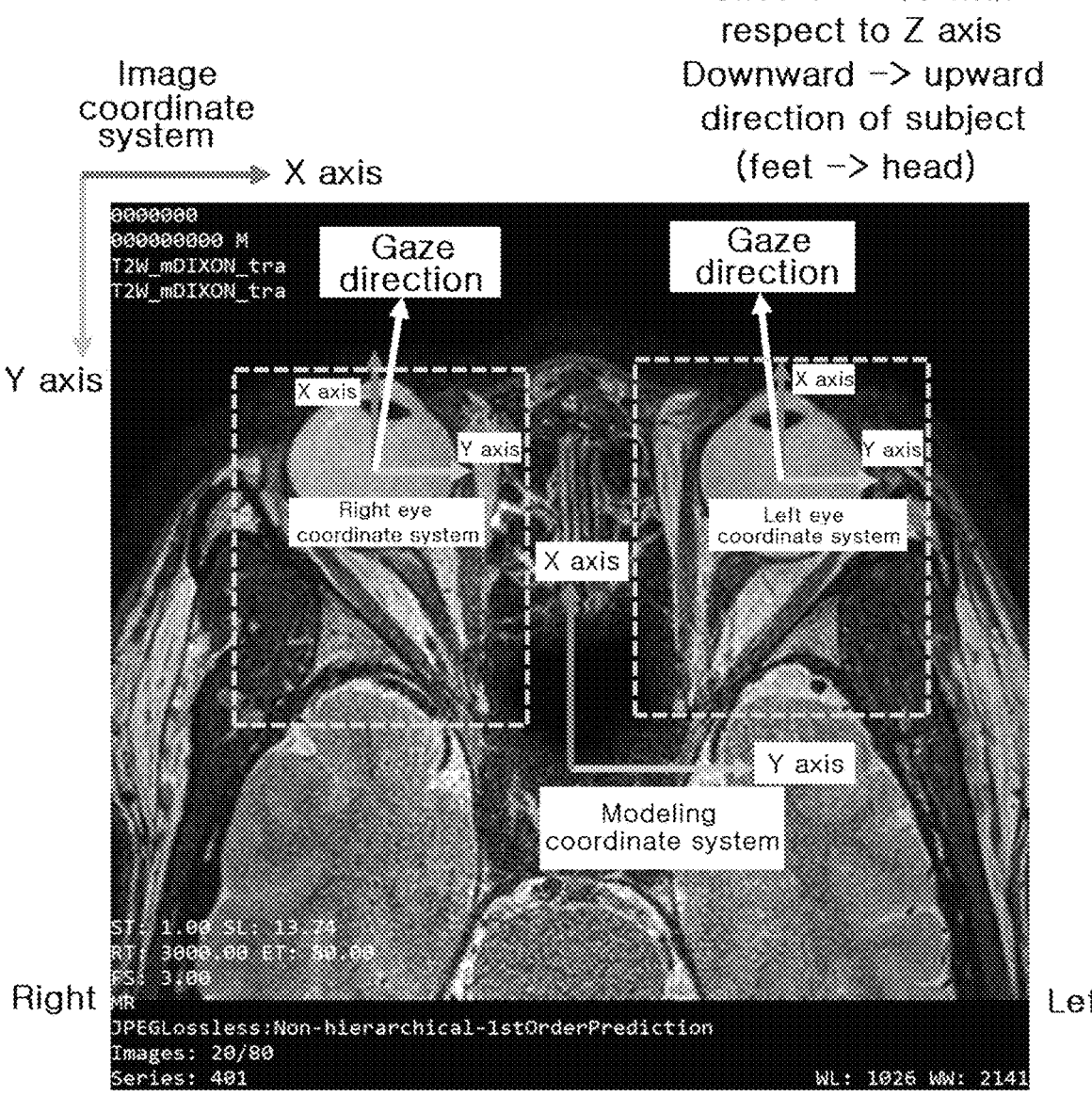
FIG. 3 is a diagram showing a first MRI head image sliced in the XY plane.
Figure 4:
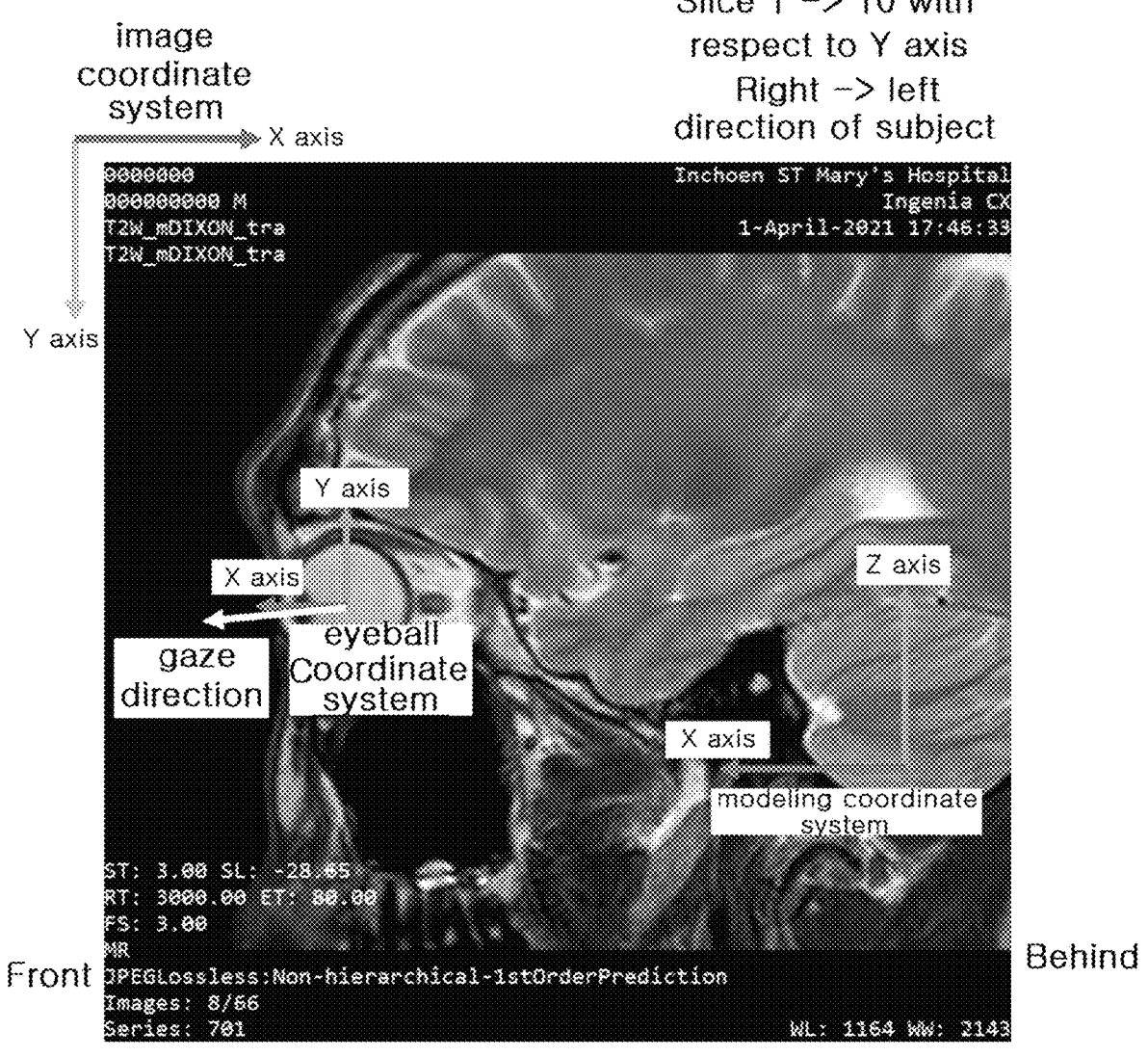
FIG. 4 is a diagram showing a second MRI head image sliced in the XZ plane.

FIG. 3 is a diagram showing the first MRI head image sliced in the XY plane. FIG. 4 is a diagram showing the second MRI head image sliced in the XZ plane. FIG. 5(A) is a diagram showing the first MRI head image with a largest eyeball among the plurality of first MRI head images sliced in the XY plane. FIG. 5(B) is a diagram showing the second MRI head image with a largest eyeball among the plurality of second MRI head images sliced in the XZ plane.

In step (a3), the first MRI head image with the largest eyeball is selected from the plurality of first MRI head images, and the selected first MRI head image is shown in FIG. 5(A).

In addition, the plurality of first MRI head images for this purpose are imaged to be sliced in the XY plane as shown in FIG. 3.

In step (a4), the second MRI image with the largest eyeball is selected from the plurality of second MRI head images, and the selected second MRI head image is shown in FIG. 5(B). For this purpose, the plurality of second MRI head images are imaged to be sliced in the XZ plane as shown in FIG. 4.

FIGS. 6(A) and (B) are conceptual diagrams showing the elements that constitute an eyeball and an optic nerve and optic nerve measurement points. FIGS. 7(A) and (B) are conceptual diagrams showing optic nerve measurement points. FIG. 8 is a diagram showing the results of analysis of the elements that constitute an eyeball and an optic nerve.

The step (b) comprises the steps of (b1) selecting an MRI head image with a larger inscribed circle inscribed on the eyeball among the first and second MRI head images having the largest eyeball, and (b2) obtaining the center of the inscribed circle, the diameter of the inscribed circle, a pair of ASCOs, and the centers of the pair of ASCOs from the MRI head image with the larger inscribed circle.

In step (b1), among a first inscribed circle (C1), a second inscribed circle (C2) and a third inscribed circle (C3) inscribed in each eyeball among the first MRI head image and the second MRI head image shown in FIGS. 5(A) and (B), the MRI head image with the larger inscribed circle is selected, and in the present invention, the third inscribed circle (C3) is determined to be the largest and the second MRI head image is selected.

Next, in step (b2), the third inscribed circle (C3) inscribed in the eyeball of the second MRI head image shown in FIG. 5(B), the center (CP3) of the third inscribed circle (C3), and the diameter of the third inscribed circle (C3), a pair of ASCOs, and the centers of the pair of ASCOs are obtained.

Referring to FIGS. 6(A) and (B) in relation to the pair of ASCOs described above, the eyeball near the optic disk includes the retina, sclera, lamina cribrosa, and optic nerve (Dura) and Pia.

In particular, referring to FIGS. 6(A) and (B) and FIGS. 7(A) and (B), the optic nerve measurement points are set as Retinal Peak (RP) (1) and Bruch's Membrane Opening (BMO) (2), Anterior Scleral Canal Opening (ASCO) (3), Posterior Scleral Canal Opening (PSCO) (4), Anterior-most aspect of the SubArachnoid Space (ASAS) (5), Dura Path (DP) (6), Optical Nerve Path (ONP) (7), optical nerve joint (Dura Joint) (8), and Lamina Cribrosa (LC).

In FIGS. 7 (A) and (B), the Retinal Peak (RP) (1) is indicated in red and is an arbitrary point set for the convenience of model production. For the convenience of model production on the OCT, the RP (1) is set in OCT on the protrusion of retina (set in OCT).

Next, in FIGS. 7(A) and (B), the Bruch's Membrane Opening (BMO) (2) is set at the end of Bruch's membrane (set in OCT), which appears characteristically bright on OCT.

Next, in FIGS. 7(A) and (B), the Anterior Scleral Canal Opening (ASCO) (3) is indicated in green and is set at both ends of the canal on the outer surface of the choroid on OCT, and set at both ends of the canal on the inner surface of the sclera on MRI (set in MRI, OCT).

In the present invention, the Anterior Scleral Canal Opening (ASCO) (3) becomes the standard for matching the ASCO set in the second MRI head image and the ASCO set in the corrected OCT cross-sectional image of the eyeball (a reference for connecting OCT and MRI measurement points) when matching the corrected OCT cross-sectional image of the eyeball to the second MRI head image.

In FIGS. 7(A) and (B), the Posterior Scleral Canal Opening (PSCO) (4) is indicated in green and is set at both ends of the scleral opening (set on MRI), but may not be clearly distinguished in some cases.

If it is not clearly distinguished, the PSCO (4) is set on the outer surface of the sclera (Sclera) by moving the ASCO (3) in the direction of the thickness of the sclera.

Next, in FIGS. 7(A) and (B), the Anterior-most aspect of the SubArachnoid Space (ASAS) (5) is indicated in purple, and is set at the end of the sclera fiber ring, which is the point where the thin sclera around the canal opening begins to thicken, and is identified on MRI, but may not be clearly distinguished in some cases.

If it is not clearly distinguished, the ASAS (5) is set to the same point as the optic nerve path (Dura Path) (6).

Next, in FIGS. 7(A) and (B), the optic nerve path (Dura Path (DP)) (6) is indicated in dark blue and is an arbitrary point set for the convenience of model production. It is the intersection of the extension of the outer surface of the sclera and the inner surface of the optic nerve (Dura).

In addition, the optic nerve path (Dura Path(DP)) (8) is set at the connection point between the optic nerve (Dura) and the sclera on MRI, and if it is not clearly distinguished, the ASAS is set to the corresponding point.

Next, in FIGS. 7(A) and (B), the Optical Nerve Path (ONP) (7) is indicated in blue, is an arbitrary point set for the convenience of model production, and is set on the path of the optic nerve.

In particular, the Optical Nerve Path (ONP) (7) is set at the junction where the optic nerve on the MRI is in contact with the OCT image for convenience in model production, but may be seen (felt visible) on OCT in very rare cases.

The Optical Nerve Path (ONP) (7) described above may be omitted in some cases.

Next, in FIGS. 7(A) and (B), the optic nerve joint (Dura Joint) 8 is indicated in orange and is the outline where the optic nerve (Dura) and the sclera meet.

Next, in FIGS. 7(A) and (B), the Lamina Cribrosa (LC) is a line marking of the Lamina Cribrosa seen on OCT, and is compared by matching it to MRI.

The structural analysis disclosed in Wang's paper in relation to the structure of the eyeball described above is shown in FIG. 8.

FIG. 9 is a diagram showing an OCT eyeball image. FIG. 10 is a diagram showing the OCT cross-sectional image of an eyeball taken along the center line of the OCT cross-sectional image of an eyeball in FIG. 9. FIG. 11 is a diagram showing the OCT cross-sectional image of an eyeball taken along the center line in FIG. 9.

Referring to FIGS. 9 to 11, the step (c) comprises the steps of (c1) obtaining the OCT eyeball image by capturing the eyeball, (c2) generating a central line passing through the center of the optic disk of the eyeball using an OCT program, and (c3) obtaining an OCT cross-sectional image of the eyeball along the center line in the OCT eyeball image.

In step (c1), the OCT eyeball image is obtained by capturing the eyeball as shown in FIG. 9.

Next, in step (c2), the OCT eyeball image captured as shown in FIG. 10 is applied to the OCT program, and as shown in FIG. 9, an optic disk area (S1), a center (CP) and central line (CL) of the eyeball are indicated on the OCT eyeball image captured by the OCT program.

Next, in step (c3), the OCT cross-sectional images of the eyeball as shown in the lower part of FIG. 10 and FIG. 11 are obtained along the center line (CL) in the OCT eye images shown in FIGS. 9 and 10.

In this case, the OCT cross-sectional image of the eyeball is an OCT B-Scan image assuming that the center of Bruch's Membrane Opening (BMO) is the center of the optic nerve.

In particular, the OCT cross-sectional image of the eyeball is a raw data image and uses a 1:1 scale image.

The determination of the center line (CL) uses the reference of the OCT program (green cross reference).

In addition, the image accumulation of the OCT cross-sectional images of the eyeball is 12 mm in width, 9 mm in height, and 2.54 mm in depth, and the raw data image is 12 mm in width and 2.54 mm in depth.

FIG. 12 is a diagram showing the production of a high-resolution model in an OCT observation area by stacking the OCT cross-sectional images of an eyeball in an MRI coordinate system. FIG. 13 is a diagram showing an example of a high-resolution form captured by OCT in an OCT observation area. FIG. 14 is a diagram showing modeling of an OCT dark area using MRI.

In addition, the OCT B-Scan image may be stacked in the MRI coordinate system as shown in FIG. 12 and used to produce a high-resolution model in the OCT observation area.

In addition, FIGS. 13 and 14 exemplarily show modeling of the OCT dark area using the MRI.

FIGS. 15(A), (B), (C), and (D) are diagrams showing the process of correcting distortion of the OCT cross-sectional images of an eyeball.

The step (d) comprises the steps of (d1) applying the OCT cross-sectional image of the eyeball to a simplified eye model, (d2) obtaining a nodal length (NL) based on the axial length measured in an MRI head image with a larger eyeball among the first MRI head image and second MRI head image having the largest eyeball, (d3) obtaining a relative nodal length using the nodal length, (d4) obtaining a refraction half-angle αsing the relative nodal length, and (d5) correcting distortion of the OCT cross-sectional image of the eyeball using the refractive half-angle.

Referring to FIG. 15(A), in step (d2), the axial length is measured in the second MRI head image shown in FIG. 5(B) using a simplified eye model, and then the nodal length (NL) is obtained by applying [Equation 1] below to the measured axial length.

$$\text{Nodal length} = \text{Axial length}/\text{Refractive index of anterior segment}$$

$$(\text{anterior segment} = 1.333) \qquad [\text{Equation 1}]$$

Next, referring to FIG. 15(B), in step (d3), the relative nodal length is obtained by reflecting the nodal length in [Equation 2] below.

$$\text{Relative nodal length} = \text{Nodal length} \times \cos(A \sin(B\text{-Scan image height}/\text{nodal length})) \qquad [\text{Equation 2}]$$

Next, referring to FIG. 15(C), in step (d4), the reflective half-angle is obtained by reflecting the relative nodal length in [Equation 3] below.

$$\text{Reflective half-angle} = A \sin(0.5 \times \text{image width}/\text{relative nodal length}) \qquad [\text{Equation 3}]$$

Next, referring to FIG. 15(D), in step (d5), a corrected OCT cross-sectional image of the eyeball is obtained by reflecting a corrected refractive half-angle in which the refractive half-angle in [Equation 4] below is reflected to the OCT cross-sectional image of the eyeball.

$$\text{Corrected reflective half-angle} = 2 \times \text{reflective half-angle} \qquad [\text{Equation 4}]$$

FIGS. 16(A), (B), and (C) are diagrams showing the process of arranging and aligning the OCT cross-sectional image of an eyeball in the process of correcting distortion of the OCT cross-sectional image of an eyeball. FIGS. 17(A), (B), (C), and (D) are diagrams showing points used in modeling in the process of correcting distortion of the OCT cross-sectional images of an eyeball.

Hereinafter, with reference to FIGS. 16 and 17, the process of correcting the distortion of the OCT cross-sectional image of the eyeball related to [Equation 1] to [Equation 4] will be described in detail.

In FIG. 16(A), the gaze direction axis is set by connecting the anterior vertex (red dot) of the eyeball and the posterior vertex (yellow dot) of the lens in the axial and sagittal images, where the lens of the eyeball is at its maximum size in the MRI image.

Next, the point that progresses along the gaze direction as much as the focal length (dark yellow line) from the intersection of the gaze direction axis and the posterior part of the eyeball (pink point) is set as a Nodal Point (dark blue point), and then is used for correction later by drawing a Nodal Circle (dark blue circle) from the Nodal Point and designating ASCO (light green point).

Next, the OCT B-Scan is corrected as shown in FIG. 16(B). In this case, the Nodal Point, Nodal Circle, and focal length are used for correction.

Next, FIG. 16(C) shows the verticality of matching the MRI image and the horizontal OCT. In this case, the OCT B-Scan image is matched to the OCT Merging Circle (red arc) corrected from the Nodal Circle, rather than the Nodal Circle (dark blue arc) used for correction.

In addition, the OCT image is adjusted to have a transparency of 40%, making it easy to check the degree of match. In particular, as shown in FIG. 16(C), the choroid-scleral boundary (orange line) designated in OCT is smoothly connected to the scleral boundary (pink curve) on MRI (orange circle), and the position of the ASCO is almost matched. The axis of the gaze direction can also be seen passing through the macula.

In this case, the size of the OCT was assumed to be maintained at 12 mm at the front of the OCT picture (light green arrow).

Next, reference lines connecting the center of the OCT and the Nodal Point are drawn on the Horizontal OCT and Vertical OCT (which are dark yellow line and gray line, respectively). Here, the nine reference lines of Horizontal OCT overlap and appear as one, but the reference lines of Vertical OCT are clearly distinguished.

In addition, the distance between each reference line is 0.35 mm, which is the same as the OCT acquisition interval in the OCT Merging Circle. The arranged Vertical OCT and Horizontal OCT are 9 sheets, respectively, and a total of 18 sheets are an area of $3.1 \times 3.1$ mm$^2$, where the optic disk is reconstructed (brown arrow).

FIG. 17(A) shows two types of points (BMO: yellow point, ASCO: light green point) designated in the OCT image.

FIG. 17(B) shows five types of points (ASCO (3): light green point, PSCO: green point, ASAS (5): purple point, Inner Junction of Dura (6): dark blue point, Outer Junction of Dura (8): brown dot) designated in the MRI image In FIG. 17(C), the matched MRI image and OCT image and each designated point are simultaneously expressed.

FIG. 17(D) shows producing a model by connecting designated points in three dimensions with a spline curve (coordinate system in the figure N: Nodal <-> T: Temporal, A: Anterior <-> P: Posterior)

Hereinafter, the process of correcting the matched OCT scan is described.

In the current generation of commercial OCTs, the A-Scan passes through a common pivot point and performs scanning in a fan shape along the curved surface of the posterior part of the eye, but when scanned images are displayed, a rectangular flat format is used. This difference in shape makes the OCT B-Scan image flatter than it actually is when the posterior part of the eyeball is observed.

Therefore, when matching the OCT B-Scan to an MRI image, correction for the flat distorted OCT B-Scan image is required.

In the paper, <Kuo, Anthony N et al. "of ocular shape in retinal optical coherence tomography and effect on current clinical measures." American journal of ophthalmology vol. 156, 2 (2013): 304-11. doi: 10.1016/j.ajo.2013.03.012>, a numerical method to correct distortion of OCT by simulating the entire optical system of the eyeball and an analytical method to correct distortion using a reduced eye model were presented. The paper disclosed that the analytical method effectively saves computational time and resources compared to the numerical method, while having a small difference in distortion correction.

Referring to FIG. 16(A), the line segment connecting the anterior vertex of the eyeball (red dot) and the posterior vertex of the lens (light blue dot) from the MRI image is extended to the posterior part of the eyeball (pink dot), and this straight line was defined as the "gaze direction axis" (yellow arrow).

In addition, after identifying that the center (Centroid) of the cross section of the eyeball passes through the gaze direction axis (black and red dot), the length from the anterior vertex of the eyeball to the posterior part of the eyeball was measured as the axial length.

The focal length was calculated from the axial length using the following equation.

$$d_f = AXL/n \qquad \text{[Equation 5]}$$

($d_f$: focal length of an eyeball, AXL: axial length, n: refractive index of an eyeball (about 1.33))

Next, in order to correct OCT B-Scan, the optical cause of distortion is simulated with a reduced eye model. Starting from the nodal point of the eyeball (dark blue point in FIGS. 16(A), (B)), a virtual circle is scanned with the radius being the distance to the posterior pole (df in FIGS. 16(A), (B)) for modeling. This virtual circle with the focal length (df) as the radius is defined as a nodal circle and used for distortion correction (dark blue circle in FIGS. 16(A) and (B)).

In order to match the scale of the OCT image after correction, a reference length is needed, and in this study, the length of the upper edge of the OCT B-Scan is assumed to be the reference. It is assumed that the horizontal length of the upper edge of the OCT B-Scan is maintained at a constant length d1 (light green arrow in FIG. 16(B)) both before and after correction.

From the relationship between the Nodal Circle and the OCT B-Scan, the equation needed to obtain the image bending center angle θ (band) required for distortion correction of the OCT B-Scan image can be obtained as follows (FIG. 16(B)).

$$\theta_{(band)} = 2 \times \text{ArcSin}\left(\frac{d_1}{2} \times df\right) \qquad \text{[Equation 6]}$$

(θ(band): Image bending center angle, $d_1$: B-Scan image upper width=B-Scan image width before correction)

Here, the value of $d_1$ is 12 mm for Horizontal OCT and 9 mm for Vertical OCT.

In order to accurately scale and match the OCT B-Scan image to the MRI image in the CAD program, the lower edge of the B-Scan image (Posterior direction in the B-Scan image) is adjusted for distortion and an increased length d2 (light blue arrow in FIG. 16(B)) is required.

This is because that the a three-dimension program (Solid Edge 2020) to implement the above only handles rectangular images, cannot directly model the curved corrected B-Scan image, and treats the rectangular background circumscribed to the curved OCT B-Scan image as a transparent image.

Calculating under the assumption that the vertical length of the OCT B-Scan image before correction is 2.54 mm in the used OCT equipment and that the length of $d_1$ is maintained, the length of the lower part of the B-Scan image, d2, may be obtained through the following process. An isosceles triangle with both sides as $d_f$ and the base as $d_1$ (left in FIG. 16(B)) is drawn, and the height of the isosceles triangle is a.

The hypotenuse $d_f$ of the isosceles triangle is parallel to the side surface of the distortion-corrected OCT B-Scan image (right in FIG. 16(B)), so the proportional equation a: $d_{1/2}$=a+2.54: d2/2 is established. In this proportional equation, a is changed to the Cosine expression for $d_f$, and the proportional equation is summarized as follows.

$$d_2 = \left(d_f \times \mathrm{Cos}\left(\frac{\theta_{(band)}}{2}\right) + 2.54\right) \times \left(\frac{d_1}{d_f \times \mathrm{Cos}\left(\frac{\theta_{(band)}}{2}\right)}\right) \quad [\text{Equation 7}]$$

(d2: B-Scan image posterior width, 2.54: B-Scan image scan depth before correction)

In this case, since the value of $d_1$ is different for Horizontal and Vertical, the value of d2 is also calculated for Horizontal B-Scan and Vertical B-Scan, respectively. The size scale of the corrected B-Scan image is adjusted using the values of $d_1$ and $d_2$.

Hereinafter, the process of merging MRI images and OCT images will be described.

The OCT A-Scan light scans 2.54 mm above and below the macula. Since the Nodal circle is drawn from the scleral border of the MRI, an error occurs as much as the depth from the upper edge of the OCT B-Scan to the choroid-scleral border. The error for the position difference between the MRI Scan and the OCT Scan is defined as doffset (Red arrow in B in FIG. 16(B)). The error is corrected by advancing the nodal circle horizontally by the doffset along the gaze direction axis. This circle is defined as the OCT Merging Circle (red circle, FIG. 16(C)).

When matching the OCT B-Scan to the OCT Merging Circle, first the B-Scan image including the Optic Disc Center specified by the OCT Program Intrinsic Software is set as the reference Horizontal B-Scan and Vertical B-Scan and matched to a cross shape (FIG. 17(D)), and using this reference, the B-Scan images are used to align the match positions of the remaining B-Scan images.

After the distortion-corrected reference B-Scans are each matched to the OCT Merging Circle, the boundaries of the optic disk, macula, and sclera captured in the MRI and OCT images are compared and aligned.

The OCTs arranged in this way are arranged on the basis of 0.35 mm as described above. In the horizontal direction and the vertical direction, 4 reference OCT B-Scan images are used front and back, so 9 horizontal and 9 vertical OCT B-Scan images are used. The range of the optic disk model reconstructed by the OCT B-Scans used is a square-shaped area of 3.1 mm×3.1 mm centered on the optic disk (brown arrow in FIG. 16(C)).

To directly correct the flattening distortion of OCT B-Scan by editing the image, Python (Van Rossum, G., & Drake, F. L. (2009). Scotts Valley, CA, USA: CreateSpace.) and ImageMagick (The ImageMagick Development Team (2021). ImageMagick. Retrieved from https://imagemagick.org) are used in conjunction with the image tool.

However, distortion may occur in the process of bending the image during distortion correction. In order to identify this distortion, the values of $d_1$ of the image before and after correction are compared. The difference in size of $d_1$ before and after correction results in an error of less than 0.02 mm. This is a sufficiently small value compared to other factors, and it is determined that the distortion caused by the correction process can be ignored.

The process of verifying the matching of MRI images and OCT images will be described.

FIG. 17(C) is a photograph matching MRI and reference Horizontal B-Scan images. To facilitate comparison between MRI images and OCT images, the transparency of the OCT B-Scan image is set to 40%. The suitability of the match is verified by comparing the following three factors.

First, the position of the ASCO specified in the MRI and the position of the ASCO in the OCT B-Scan are consistent (light green dot in FIG. 16(C)).

Second, the choroid-scleral interface captured in the OCT B-Scan image matches the scleral interface in the MRI (orange circle).

Third, the posterior part of the eyeball specified in FIG. 16(A) (pink dot in FIG. 16(C)) is also on the macula captured in the OCT B-Scan image (pink circle).

The suitability is verified for matching MRI images and OCT images by comparing the above three factors.

The corrected OCT cross-sectional image of the eyeball has a predetermined curvature so that it can be matched to the second MRI head image.

FIGS. 18(A) and (B) are diagrams showing forming an inscribed circle and intersection point of an eyeball in an MRI head image with a larger eyeball among first and second MRI head images. FIG. 19 is a diagram showing the process of obtaining an intersection point for merging corrected OCT cross-sectional images of an eyeball. FIGS. 20(A) and (B) are diagrams showing obtaining an intersection point from a MRI head image with a larger eyeball among first and second MRI head mages and then merging the corrected OCT cross-sectional images of an eyeball to the obtained intersection point. FIG. 21(A) is a diagram showing obtaining the coordinates of the match part of the center point of the optic nerve and the optic disk. FIG. 21(B) is a diagram showing the process of merging the corrected OCT cross-sectional images of an eyeball. FIGS. 22(A), (B), and (C) are diagrams showing the process of merging the corrected OCT cross-sectional image of an eyeball with an MRI head image. FIGS. 23(A) and (B) are diagrams showing matching the corrected OCT cross-sectional image of an eyeball onto an MRI head image with a larger eyeball among first and second MRI head images.

Referring to FIGS. 18 to 23, the step (e) comprises the steps of (e1) forming an inscribed circle in the XY plane based on the center of the inscribed circle in an MRI head image with a larger inscribed circle, (e2) forming a first connection line connecting the center of the inscribed circle formed in the XY plane and the center of a pair of ASCOs, (e3) forming an inscribed circle in the XZ plane to include the first connection line, and (e4) merging the corrected OCT cross-sectional image of the eyeball at the intersection point where the inscribed circle formed in the XY plane, the inscribed circle in the XZ plane, and the first connection line intersect.

In step (e1), as shown in FIG. 5(A) and FIG. 18(A), the inscribed circle inscribed in the eyeball is formed in the MRI head image sliced in the XY plane.

Next, in step (e2), as shown in FIGS. 7(A) and (B), FIG. 19, and FIG. 20(A), the first connection line connecting the center of the inscribed circle formed in the XY plane A and the center of a pair of ASCOs is formed (see FIG. 19 and FIG. 20(A)).

Next, in step (e3), the inscribed circle is formed in the XZ plane to include the first connection line, as shown in FIG. 19 and FIG. 20(A).

Next, in step (e4), as shown in FIG. 18(B) and FIG. 20(B), the corrected OCT cross-sectional image of the eyeball is matched to the intersection point where the inscribed circle formed in the XY plane, the inscribed circle in the XZ plane and the first connection line intersect.

In particular, referring to FIGS. 21(A) and (B), in step (e4), the center point of the optic nerve (Dura) is obtained from the first MRI head image slid in the XY plane and the second MRI head image slid in the XZ plane, and then, the coordinates for the intersection point, which is the match part of the optic disk, is obtained in three-dimensionally.

In this case, the intersection point becomes the center of the line connecting the pair of ASCOs shown in FIGS. 7(A) and (B).

Accordingly, the corrected OCT cross-sectional image of the eyeball at the intersection point of the MRI head image are matched and combined as shown in FIG. 20(B), FIGS. 22(A), (B), and (C), and FIGS. 23(A) and (B).

FIGS. 24(A) and (B) are diagrams showing the formation of a plurality of inscribed circles in an MRI head image with a larger eyeball among first and second MRI head images.

After performing step (e), as shown in FIGS. 24(A) and (B), the inscribed circle of the MRI head image and the inscribed circle of the corrected OCT cross-sectional image of the eyeball are drawn and then, the difference in radius between the respective inscribed circles is compared.

In this case, since the eyeball is not exactly spherical, the inscribed circle in the MRI head image is drawn in the area that overlaps with the OCT cross-sectional image of the eyeball corrected only for the occipital area, and the inscribed circle in the OCT cross-sectional image of the eyeball is drawn based on Bruch's Membrane. The results are shown in [Table 1] and [Table 2] below.

TABLE 1

| Subject/eye | Original | Numerical (ray traced) | Analytical (reduced eye) | MRI |
|---|---|---|---|---|
| 1/OD | 69.30 | 14.92 | 16.02 | 12.04 |
| 1/OS | 40.66 | 13.23 | 13.01 | 11.46 |
| 2/OD | 17.54 | 10.01 | 8.37 | 12.24 |
| 2/OS | 24.15 | 11.18 | 8.74 | 12.97 |
| 3/OD | 98.31 | 15.37 | 21.04 | 12.42 |
| 3/OS | 128.95 | 14.62 | 21.22 | 12.92 |
| 4/OD | 31.55 | 10.94 | 11.13 | 10.61 |
| 4/OS | 51.38 | 12.58 | 12.25 | 11.02 |
| 5/OD | 52.51 | 15.40 | 14.12 | 12.30 |
| 5/OS | 134.13 | 17.81 | 13.83 | 12.32 |

TABLE 2

| | | | | radius of inscribed circle | | | | |
|---|---|---|---|---|---|---|---|---|
| | | | | MRI | OCT | Error | Error % | Note |
| Sagittal | 7 | Right | 1 | 20.7 | 18.5 | 2.2 | 10.62802 | MRI |
| | 8 | eye | 2 | 20.32 | 19.31 | 1.01 | 4.970472 | shot is |
| | 9 | Left | 3 | 21.76 | 23.69 | −1.93 | −8.86949 | blurry |
| | 25 | eye | 1 | 12.69 | 21.93 | −9.24 | −72.8132 | |
| | 26 | | 2 | 21.08 | 19.82 | 1.26 | 5.97723 | |
| | 27 | | 3 | 20.6 | 19.17 | 1.43 | 6.941748 | |
| Axial | 1819 | Left | 1 | 18.74 | 18.19 | 0.55 | 2.934899 | MRI |
| | 20 | eye | 2 | 16.98 | 18.62 | −1.64 | −9.65842 | shot is |
| | 21 | | 3 | 22.22 | 18.36 | 3.86 | 17.37174 | blurry |
| | 22 | | 4 | 20.02 | 17.78 | 2.24 | 11.18881 | |
| | 23 | | 5 | 19.06 | 17.21 | 1.85 | 9.706191 | |
| | 24 | | 6 | 17.53 | 17.29 | 0.24 | 1.369082 | |
| | 25 | | 7 | 23.52 | 17.32 | 6.2 | 26.36054 | |
| | | | 8 | 18.02 | 17.4 | 0.62 | 3.440622 | |
| | 1819 | right | 1 | 19.95 | 19.53 | 0.42 | 2.105263 | MRI |
| | 20 | | 2 | 19.6 | 17.85 | 1.75 | 8.928571 | shot is |
| | 21 | | 3 | 20.58 | 17.44 | 3.14 | 15.25753 | blurry |
| | 22 | | 4 | 19.4 | 17.23 | 2.17 | 11.18557 | |
| | 23 | | 5 | 21.57 | 17.53 | 4.04 | 18.72972 | |
| | 24 | | 6 | 19.83 | 17.42 | 2.41 | 12.1533 | |
| | 25 | | 7 | 23.42 | 17.35 | 6.07 | 25.91802 | |
| | | | 8 | 19.13 | 17.08 | 2.05 | 10.71615 | |

FIGS. 25(A) and (B) are diagrams showing the process of forming an ASCO on a corrected OCT cross-sectional image of an eyeball. FIGS. 26(A) and (B) are diagrams showing the process of forming a lamina cribrosa on a corrected OCT cross-sectional image of an eyeball. FIG. 27 is a diagram showing the included angle in the image shown in FIG. 22 (A). FIG. 28 is a diagram showing the formation of BMO, choroid opening, and ASCO in a corrected OCT cross-sectional image of an eyeball. Referring to FIGS. 25 to 28, the present invention further comprises the step of three-dimensionally modeling the ASCO model on the corrected OCT cross-sectional image of the eyeball between step (f) and step (g).

In particular, the step of three-dimensional modeling the ASCO model on the corrected OCT cross-sectional image of the eyeball comprises the steps of displaying Bruch's Membrane Opening (BMO), Choroid Opening, and the ASCO on the OCT cross-sectional image of the eyeball, respectively, forming the line segments (red, light blue, blue, and green line segments shown in FIGS. 25(A) and (B)) to distinguish the Bruch's Membrane Opening (BMO), the Choroid Opening, and the ASCO in the corrected OCT cross-sectional image of the image, as shown in FIGS. 25(A) and (B), forming a normal line (black normal line) passing through the center point of the line segment and then forming a vertical plane perpendicular to the normal line, and three-dimensionally modeling the ASCO model by connecting the vertical plane through which the central part is penetrated and the line segment of the ASCO, as shown in FIG. 25(B).

In the step of modeling the ASCO model in three-dimensions by connecting the vertical plane through which the central part penetrates and the line segment of the ASCO, the vertical plane through which the central part penetrates is formed by referring to the OCT cross-sectional image of the eyeball sliced on the XY plane and the OCT cross-sectional image of the eyeball sliced on the XZ plane.

The images to which the ASCO model is applied to the OCT cross-sectional image of the eyeball corrected through the above steps are shown in FIG. 27 and FIGS. 28(A) and (B).

The shapes and related parameters (major axis, minor axis, eccentricity, included angle, and inter-axial distance) of the optic disk and optic nerve (Dura) obtained from the images shown in FIG. 27 are shown in [Table 3] below.

TABLE 3

|  | Optic disk | Optic nerve (Dura) |
| --- | --- | --- |
| Shape | symmetrical ellipse | asymmetric ellipse |
| Major axis | 1.57 mm | 9.87 mm |
| Minor axis | 1.44 mm | 4.88 mm |
| Eccentricity | 0 | 1.19 mm |
| Included angle | 66.39° |  |
| Inter-axial distance | 0.1 mm |  |

In addition, referring to FIGS. 26(A) and (B), the present invention may further comprise the step of modeling Lamina Cribrosa (LC) in three-dimension on the OCT cross-sectional image of the eyeball after the step of modeling the ASCO model in three-dimensions on the corrected OCT cross-sectional image of the eyeball. The step of modeling the Lamina Cribrosa (LC) on the OCT cross-sectional image of the eyeball comprises the steps of forming a cross-section of the Lamina Cribrosa (LC) on the OCT cross-sectional image of the eyeball, forming a reference plane to form the Lamina Cribrosa (LC), and three-dimensionally modeling the Lamina Cribrosa (LC) from the reference plane.

FIGS. 29 and 30 are diagrams showing three-dimensional modeling of an eyeball model in an MRI head image with a larger eyeball among first and second MRI head images.

Referring to FIGS. 29 and 30, the step (f) comprises the steps of (f1) forming a gaze reference line connecting the center of the eyeball and the center of the iris in the MRI head image with the larger inscribed circle inscribed in the eyeball, among the first and second MRI head images having the largest eyeball, (f2) forming a plurality of first reference planes perpendicular to the gaze reference line, (f3) forming a plurality of first ellipses on the plurality of first reference planes spaced apart from each other, respectively, (f4) forming an ocular surface surrounding the plurality of first ellipses, (f5) forming the BMO with a thickness of 0.004 mm from the inner surface of the ocular surface, (f6) sequentially forming the choroid and sclera with a predetermined thickness from the outer surface of the ocular surface, and (f7) generating the three-dimensionally modeled eyeball model.

Hereinafter, the plurality of first ellipses may be asymmetric ellipses of different sizes.

FIGS. 31(A) and (B) are diagrams showing the process of three-dimensionally modeling an optic nerve model. FIGS. 32(A) and (B) are diagrams showing a three-dimensionally modeled optic nerve model. FIG. 33 is a diagram showing an eyeball model and an optic nerve model. FIG. 34 is a diagram showing measurement of the axial length, straight line distance from the center of the filiform plate to the optic nerve root, left and right widths dividing the straight line distance into five equal parts, ratio of the straight line distance to the cochlear width, curve connecting the centers of the left and right widths, and length of the curve in a state where the corrected OCT cross-sectional image of an eyeball is matched onto the MRI head image with a larger eyeball among first and second MRI head images. FIG. 35 is a cross-sectional perspective view showing an optic nerve model.

Referring to FIGS. 31 to 35, the step (g) comprises the steps of (g1) obtaining the center point of the optic nerve root based on the first and second MRI head images having the largest eyeball, (g2) forming a second connection line connecting a pair of ASCOs and the center point of the optic nerve root, (g3) forming a plurality of second reference planes dividing the second connection line into five parts, (g4) forming a plurality of second ellipses on a plurality of second reference planes using the first MRI head image and the second MRI head image, (g5) forming a reference line connecting the centers of the plurality of second ellipses, (g6) forming an optic nerve path surrounding the plurality of second ellipses, (g7) extending the end of the optic nerve path to the sclera, (g8) forming the interior of the optic nerve path by reflecting a preset thickness of the optic nerve path, and (g9) forming the three-dimensionally modeled optic nerve model.

Referring to FIGS. 31(A) and (B), in step (g3), the second reference plane refers to the horizontal length and vertical length, respectively, by comparing the MRI images sliced in the XY plane and XZ plane, and it is assumed that the first, second, third, fourth, fifth, and sixth surfaces are ellipses, the horizontal lengths are substituted by referring to [Table 4] below.

TABLE 4

| Surface | Horizontal length | Vertical length |
| --- | --- | --- |
| First surface | 6.86 | 4.65 |
| Second surface | 4.03 | 4.54 |
| Third surface | 4.18 | 2.43 |
| Fourth surface | 4.6 | 2.41 |
| Fifth surface | 5.3 | 2.97 |
| Sixth surface | 4.65 | 4.14 |

The optic nerve model which is three-dimensionally modeled through step (g) is as shown in FIG. 32. In addition, the eyeball model and optic nerve model three-dimensionally modeled according to the present invention are as shown in FIG. 33, and as shown in FIG. 34, the axial length, straight line distance from the center of the filiform plate to the optic nerve root, left and right widths dividing the straight line distance into five equal parts, ratio of the straight line distance to the cochlear width, curve connecting the centers of the left and right widths, and length of the curve may be measured in a state where the corrected OCT cross-sectional image of an eyeball is matched onto the MRI head image with a larger eyeball among first and second MRI head images.

In addition, in the cross section of the optic nerve model shown in FIG. 35, the first distance (A) from the center of the cross section in the long axis to the left end, the second distance (B) from the center of the cross section in the long axis to the right end, and the third distance (C) from the center of the cross section in the short axis to the upper end, the fourth distance (D) from the center of the cross section in the short axis to the lower end, a ratio of the second distance (B) to the first distance (A), a ratio of the fourth distance (D) to the third distance (C) are as shown in [Table 5] below.

TABLE 5

| First distance (A) | 3.5 |
| --- | --- |
| Second distance (B) | 5.95 |
| Third distance (C) | 2.31 |
| Fourth distance (D) | 2.62 |
| Ratio (B/A) of second distance (B) to first distance (A) | 1.7 |
| Ratio (D/C) of fifth distance (D) to third distance (C) | 1.13 |

2. Method for Three-Dimensionally Modeling an Eyeball and an Optic Nerve Using a Merge of MRI Images and OCT Images Hereinafter, with reference to FIGS. 2 to 7 and 23 to 36, a method for three-dimensionally modeling an eyeball and an optic nerve using a merge of MRI images and OCT images according to an embodiment of the present invention will be described.

In particular, a method for three-dimensionally modeling an eyeball and an optic nerve using a merge of MRI images and OCT images according to an embodiment of the present invention subdivides and specifies the technical content covered in steps (e) to (g), which have been described in the method for generating an optic nerve path using a match of MRI images and OCT images as described above.

FIG. 36 is a flowchart showing a method for three-dimensionally modeling an eyeball and an optic nerve using a merge of an MRI image and an OCT image according to an embodiment of the present invention.

Referring to FIG. 36, a method for three-dimensionally modeling an eyeball and an optic nerve using a merge of an MRI image and an OCT image according to an embodiment of the present invention comprises the steps of (a) three-dimensionally modeling an eyeball model based on a shape of an eyeball in first and second MRI head images (S100); (b) three-dimensionally modeling an ASCO model in a corrected OCT cross-sectional image of the eyeball (S200); (c) three-dimensionally modeling lamina cribrosa (LC) in a corrected OCT eyeball image (S300); and (d) generating an optic nerve model by three-dimensionally modeling an optic nerve path connected to the three-dimensionally modeled eyeball model (S400).

In step (a), the first MRI head image is an MRI head image which has the largest eyeball shown in FIG. 3 and FIG. 5(A) among the plurality of first MRI head images each sliced in the XY plane shown in FIG. 2.

In addition, in step (a), the second MRI head image is an MRI head image which has the largest eyeball shown in FIG. 3 and FIG. 5(B) among the plurality of second MRI head images each sliced in the XZ plane shown in FIG. 2.

In particular, the step (a) comprises the steps of (a1) forming a gaze reference line passing through the center of the eyeball and the center of the iris in the second MRI head image with a larger inscribed circle inscribed on the eyeball, among the first MRI head image and the second MRI head image, (a2) forming a plurality of first reference planes perpendicular to the gaze reference line, (a3) forming a plurality of first ellipses on the plurality of first reference planes spaced apart from each other, and (a4) forming an ocular surface surrounding the plurality of first ellipses.

Referring to FIGS. 29(A) and (B), in step (a2), the plurality of first reference planes may be arranged to be spaced apart from each other at equal intervals, but the present invention is not limited thereto.

Next, referring to FIG. 29(B), in step (a3), a plurality of first ellipses are formed on the plurality of first reference planes. In this case, the plurality of first ellipses are formed so as to be located on the same plane as the plurality of first reference planes, referring to the eyeball shape of the plurality of first MRI head images and the eyeball shape of the plurality of second MRI head images.

In particular, the plurality of first ellipses are asymmetrical ellipses that become smaller toward both sides from the first ellipse located at the center of the eyeball among plurality of first ellipses, based on the eyeball shape of the plurality of first MRI head images and the eyeball shape of the plurality of second MRI head images.

Next, in step (a4), an ocular surface surrounding the plurality of first ellipses by connecting the plurality of first ellipses along the gaze reference line is formed.

Next, referring to FIGS. 30(A) and (B), the step (a) further comprises, after step (a4), the steps of (a5) forming a BMO layer with a thickness of 0.004 mm from an inner surface of the ocular surface, (a6) sequentially forming choroid and sclera with a predetermined thickness from an outer surface of the ocular surface, and (a7) generating a three-dimensionally modeled eyeball model.

In step (a5), by applying 0.004 mm, which is a literature value for the thickness of the BMO layer, the BMO layer is formed from the inner surface of the ocular surface.

Next, in step (a6), the choroid and sclera are sequentially formed to have a predetermined thickness from the outer surface of the ocular surface by referring to the thickness of the choroid and sclera in the corrected OCT cross-sectional image of the eyeball.

After steps (a1) to (a6), the eyeball model to be implemented is three-dimensionally modeled as in step (a7).

Next, the step (b) comprises the steps of (b1) marking Bruch's Membrane Opening (BMO), Choroid Opening, and ASCO on the corrected OCT cross-sectional image of the eyeball, (b2) forming a BMO line, a choroid opening line, and an ASCO line to distinguish a Bruch's Membrane Opening (BMO) layer, a choroid opening layer, and an ASCO layer in the corrected OCT cross-sectional image of the eyeball, (b3) forming a normal line perpendicular to the BMO line, choroid opening line, and ASCO line and then forming a vertical plane perpendicular to the normal line, and (b4) three-dimensionally modeling the ASCO model by connecting the vertical plane through which a central part penetrates and the ASCO line.

Referring to FIG. 25(A), in step (b2), the BMO line (red line in FIG. 25(A)) and the choroidal opening line (light blue line in FIG. 25(A)) and the ASCO line (blue line in FIG. 25(A)) are formed on the corrected OCT cross-sectional image of the eyeball to distinguish the Bruch's Membrane Opening (BMO) layer, the choroid opening layer, and the ASCO layer.

Next, in step (b3), the normal line (black line in FIG. 25(A)) perpendicular to the BMO line, choroidal opening line, and ASCO line is formed, and then the vertical plane perpendicular to the normal line is formed.

Next, in step (b4), the ASCO model is formed as shown in FIG. 25(B).

Next, the step (c) comprises the steps of (c1) forming a cross-section of Lamina Cribrosa (LC) on the corrected OCT cross-sectional image of the eyeball, (c2) forming a reference plane for forming the Lamina Cribrosa (LC), and (c3) three-dimensionally modeling the Lamina Cribrosa (LC) from the reference plane.

In step (c1), as shown in FIG. 26(A), the cross-section of LC (Lamina Cribrosa) (purple area in FIG. 26(A)) is formed on the corrected OCT cross-sectional image of the eyeball.

Next, in step (c2), the reference plane for forming the LC (Lamina Cribrosa) is formed, and accordingly, in step (c3), the LC (Lamina Cribrosa) is three-dimensionally modeled from the reference plane as shown in FIG. 26(B) (gray area in FIG. 26(B)).

The steps (b) and (c) described above relate to three-dimensional modeling of the optic disk connecting the eyeball and the optic nerve.

Next, the step (d) comprises the steps of (d1) obtaining a center point of an optic nerve root based on the first MRI head image and the second MRI head image, (d2) forming a second connection line connecting the center point of the optic nerve root with a pair of ASCOs, and (d3) forming a plurality of second reference planes dividing the second connection line into five equal parts.

In step (d1), the center point of the optic nerve root opposite to the optic disk to which one end of the optic nerve is connected is obtained by referring to the optic nerve shape of the first MRI head image and the optic nerve shape of the second MRI head image.

Next, in step (d2), the center of the line connecting the pair of ASCOs is connected to the center point of the optic nerve root to form the second connection line (red line in FIG. 31(B)).

Next, in step (d3), the plurality of second reference planes are formed to divide the second connection line into five equal parts.

Next, the step (d) further comprises the steps of (d4) forming the plurality of second ellipses on the plurality of second reference planes based on the first MRI head image and the second MRI head image, (d5) forming a reference line connecting the centers of the plurality of second ellipses, and (d6) forming an optic nerve path surrounding the plurality of second ellipses along the reference line.

Referring to FIGS. 31(A) and (B), in step (d4), the plurality of second ellipses (first surface, second surface, third surface, fourth surface, fifth surface, sixth surface in FIGS. 31(A) and (B)) are formed with reference to the optic nerve shape of the first MRI head image and the optic nerve shape of the second MRI head image.

Next, referring to FIG. 31(B) and FIG. 32 (A), in step (d5), the reference line connecting the centers of the plurality of second ellipses is formed.

Next, referring to FIG. 31(B), in step (d6), the outer peripheral surfaces of the plurality of second ellipses are connected parallel to the reference line to form the optic nerve path surrounding the plurality of second ellipses.

Next, the step (d) further comprises the steps of (d7) extending the end of the optic nerve path to the sclera, (d8) forming the interior of the optic nerve path by reflecting a preset thickness of the optic nerve path, and (d9) forming a three-dimensionally modeled optic nerve model.

In step (d8), the thickness of the optic nerve, which is a preset thickness, is identified by referring to the optic nerve shape of the first MRI head image and the optic nerve shape of the second MRI head image, and the interior of the optic nerve path is formed by reflecting the thickness of the optic nerve.

After steps (d1) to (d8), in step (d9), the optic nerve model as shown in FIGS. 32(A) and (B) is three-dimensionally modeled.

In addition, the eyeball model and optic nerve model modeled in three dimensions according to the present invention are as shown in FIG. 33. In addition, as shown in FIG. 34, the axial length, straight line distance from the center of the filiform plate to the optic nerve root, left and right widths dividing the straight line distance into five equal parts, ratio of the straight line distance to the cochlear width, curve connecting the centers of the left and right widths, and length of the curve may be measured in a state where the corrected OCT cross-sectional image of the eyeball is matched onto the MRI head image with a larger eyeball among first and second MRI head images.

In addition, in the cross section of the optic nerve model shown in FIG. 35, the first distance (A) from the center of the cross section in the long axis to the left end, the second distance (B) from the center of the cross section in the long axis to the right end, and the third distance (C) from the center of the cross section in the short axis to the upper end, the fourth distance (D) from the center of the cross section in the short axis to the lower end, a ratio of the second distance (B) to the first distance (A), a ratio of the fourth distance (D) to the third distance (C) are as shown in [Table 6] below.

TABLE 6

| First distance (A) | 3.5 |
|---|---|
| Second distance (B) | 5.95 |
| Third distance (C) | 2.31 |
| Fourth distance (D) | 2.62 |
| Ratio (B/A) of second distance (B) to first distance (A) | 1.7 |
| Ratio (D/C) of fifth distance (D) to third distance (C) | 1.13 |

The description of the present invention is used for illustration and those skilled in the art will understand that the present invention can be easily modified to other detailed forms without changing the technical spirit or an essential feature thereof. Therefore, the aforementioned exemplary embodiments are all illustrative in all aspects and are not limited. For example, each component described as a single type may be implemented to be distributed and similarly, components described to be distributed may also be implemented in a combined form. The scope of the invention is to be defined by the scope of claims provided below, and all variations or modifications that can be derived from the meaning and scope of the claims as well as their equivalents are to be interpreted as being encompassed within the scope of the present invention.

The invention claimed is:

1. A method for three-dimensionally modeling an eyeball and an optic nerve using a merge of an MRI image and an OCT image, the method comprising:

three-dimensionally modeling an eyeball model based on a shape of the eyeball in a first MRI head image and a second MRI head image;

three-dimensionally modeling an ASCO model in the corrected OCT cross-sectional image of the eyeball;

three-dimensionally modeling a lamina cribrosa (LC) in the corrected OCT cross-sectional image of the eyeball; and generating an optic nerve model by three-dimensionally modeling an optic nerve path connected to the eyeball model, wherein the first MRI head image is a first image having a largest eyeball among a plurality of first MRI head images, each of the plurality of first MRI head images being sliced in a XY plane, and wherein the second MRI head image is a second image having a largest eyeball among a plurality of second MRI head images, each of the plurality of second MRI head images being sliced in a XZ plane, wherein the three-dimensionally modeling of the eyeball model comprises:

forming a gaze reference line passing through a center of the eyeball and a center of an iris in an MRI head image selected from the first MRI head image and the second MRI head image, the selected MRI head image having a largest inscribed circle inscribed on the eyeball;

forming a plurality of first reference planes perpendicular to the gaze reference line;

forming a plurality of first ellipses on the plurality of first reference planes, respectively, spaced apart from each other.

2. The method of claim 1, wherein the three-dimensionally modeling of the eyeball model further comprises:

forming an ocular surface surrounding the plurality of first ellipses, wherein the plurality of first ellipses are asymmetrical ellipses that become smaller toward both sides from a first ellipse located at the center of the eyeball among the plurality of first ellipses, based on an eyeball shape of the plurality of first MRI head images and an eyeball shape of the plurality of second MRI head images.

3. The method of claim 2, wherein the three-dimensionally modeling of the eyeball model further comprises:

forming a BMO layer with a thickness of 0.004 mm from an inner surface of the ocular surface;

sequentially forming a choroid and a sclera with a predetermined thickness from an outer surface of the ocular surface; and generating the eyeball model that is three-dimensionally modeled.

4. The method of claim 1, wherein the three-dimensionally modeling of the ASCO model comprises:

marking a Bruch's Membrane Opening (BMO), a choroid opening, and an ASCO on the corrected OCT cross-sectional image of the eyeball;

forming a BMO line, a choroid opening line, and an ASCO line to distinguish a Bruch's Membrane Opening (BMO) layer, a choroid opening layer, and an ASCO layer in the corrected OCT cross-sectional image of the eyeball;

forming a normal line perpendicular to the BMO line, the choroid opening line, and the ASCO line and then forming a vertical plane perpendicular to the normal line; and three-dimensionally modeling the ASCO model by connecting the vertical plane having a penetrated central part with the ASCO line.

5. The method of claim 1, wherein the three-dimensionally modeling of the lamina cribrosa comprises:

forming a cross-section of the Lamina Cribrosa (LC) on the corrected OCT cross-sectional image of the eyeball;

forming a second reference plane to form the Lamina Cribrosa (LC); and three-dimensionally modeling the Lamina Cribrosa (LC) from the second reference plane.

6. The method of claim 1, wherein the generating of the optic nerve model comprises:

obtaining a center point of an optic nerve root based on the first MRI head image and the second MRI head image;

forming a second connection line connecting the center point of the optic nerve root with a pair of ASCOs; and forming a plurality of second reference planes dividing the second connection line into five equal parts.

7. The method of claim 6, wherein the generating of the optic nerve model further comprises:

forming a plurality of second ellipses on the plurality of second reference planes, respectively, based on the first MRI head image and the second MRI head image;

forming a first reference line connecting centers of the plurality of second ellipses; and forming an optic nerve path surrounding the plurality of second ellipses along the first reference line.

8. The method of claim 7, wherein the generating of the optic nerve model further comprises:

extending an end of the optic nerve path to a sclera;

forming an interior of the optic nerve path by reflecting a preset thickness of the optic nerve path; and forming a three-dimensionally modeled optic nerve model.

9. A method for three-dimensionally modeling an eyeball and an optic nerve using a merge of an MRI image and an OCT image, the method comprising:

three-dimensionally modeling an eyeball model based on a shape of the eyeball in a first MRI head image and a second MRI head image;

three-dimensionally modeling an ASCO model in a corrected OCT cross-sectional image of the eyeball;

three-dimensionally modeling a lamina cribrosa (LC) in the corrected OCT cross-sectional image of the eyeball; and generating an optic nerve model by three-dimensionally modeling an optic nerve path connected to the eyeball model, wherein the first MRI head image is a first MRI head image having a largest eyeball among a plurality of first MRI head images, each of the plurality of first MRI head images being sliced in a XY plane, and wherein the second MRI head image is a second MRI head image having a largest eyeball among a plurality of second MRI head images, each of the plurality of second MRI head images being sliced in a XZ plane, wherein the three-dimensionally modeling of the ASCO model comprises:

marking a Bruch's Membrane Opening (BMO), a choroid opening, and an ASCO on the corrected OCT cross-sectional image of the eyeball;

forming a BMO line, a choroid opening line, and an ASCO line to distinguish a Bruch's Membrane Opening (BMO) layer, a choroid opening layer, and an ASCO layer in the corrected OCT cross-sectional image of the eyeball;

forming a normal line perpendicular to the BMO line, the choroid opening line, and the ASCO line and then forming a vertical plane perpendicular to the normal line; and three-dimensionally modeling the ASCO model by connecting the vertical plane having a penetrated central part with the ASCO line.

10. A method for three-dimensionally modeling an eyeball and an optic nerve using a merge of an MRI image and an OCT image, the method comprising:

three-dimensionally modeling an eyeball model based on a shape of the eyeball in a first MRI head image and a second MRI head image;

three-dimensionally modeling an ASCO model in a corrected OCT cross-sectional image of the eyeball;

three-dimensionally modeling a lamina cribrosa (LC) in the corrected OCT cross-sectional image of the eyeball; and generating an optic nerve model by three-dimensionally modeling an optic nerve path connected to the eyeball model, wherein the first MRI head image is a first MRI head image having a largest eyeball among a plurality of first MRI head images, each of the plurality of first MRI head images being sliced in a XY plane, and wherein the second MRI head image is a second MRI head image having a largest eyeball among a plurality of second MRI head images, each of the plurality of second MRI head images being sliced in a XZ plane, wherein the generating of the optic nerve model comprises:

obtaining a center point of an optic nerve root based on the first MRI head image and the second MRI head image;

forming a second connection line connecting the center point of the optic nerve root with a pair of ASCOs; and forming a plurality of second reference planes dividing the second connection line into five equal parts.

* * * * *